(12) United States Patent
Yoshida et al.

(10) Patent No.: US 12,112,541 B2
(45) Date of Patent: Oct. 8, 2024

(54) BED SYSTEM

(71) Applicant: PARAMOUNT BED CO., LTD., Tokyo (JP)

(72) Inventors: Mao Yoshida, Tokyo (JP); Takeshi Nagayasu, Tokyo (JP); Yosuke Yamazaki, Tokyo (JP); Junichi Tamura, Tokyo (JP)

(73) Assignee: PARAMOUNT BED CO., LTD., Tokyo (JP)

( * ) Notice: Subject to any disclaimer, the term of this patent is extended or adjusted under 35 U.S.C. 154(b) by 0 days.

(21) Appl. No.: 18/133,720

(22) Filed: Apr. 12, 2023

(65) Prior Publication Data

US 2023/0245459 A1 Aug. 3, 2023

Related U.S. Application Data

(63) Continuation of application No. 17/326,612, filed on May 21, 2021, now Pat. No. 11,657,615.

(30) Foreign Application Priority Data

Oct. 7, 2020 (JP) ................................. 2020-170023

(51) Int. Cl.
*G06V 20/52* (2022.01)
*A61B 5/00* (2006.01)
(Continued)

(52) U.S. Cl.
CPC ............ *G06V 20/52* (2022.01); *A61B 5/1115* (2013.01); *A61B 5/1117* (2013.01); *A61B 5/1128* (2013.01); *A61B 5/7275* (2013.01); *G06T 7/70* (2017.01); *G06V 40/103* (2022.01); *G06V 40/20* (2022.01); *G08B 21/0446* (2013.01); *H04N 7/18* (2013.01); *A61G 7/0507* (2013.01);
(Continued)

(58) Field of Classification Search
None
See application file for complete search history.

(56) References Cited

U.S. PATENT DOCUMENTS 9,625,884 B1 * 4/2017 Ousley .................. G16H 20/30
10,004,654 B2 * 6/2018 Zerhusen ............. A61G 12/001
(Continued)

FOREIGN PATENT DOCUMENTS

| JP | 2008-206869 | 9/2008 |
|---|---|---|
| JP | 2009-118980 | 6/2009 |

(Continued)

*Primary Examiner* — Reza Aghevli
(74) *Attorney, Agent, or Firm* — Wenderoth, Lind & Ponack, L.L.P.

(57) ABSTRACT

A bed system includes: an imaging device; a bed on which the imaging device is to be installed; and a controller configured to process an image acquired by the imaging device to predict a possibility of overturning of a user, in which, when it is determined that a state of the user is a first state, the controller predicts the possibility of overturning of the user based on a first parameter, when it is determined that the state of the user is a second state, the controller predicts the possibility of overturning of the user based on a second parameter, the first state is a state of the user different from the second state, and the first parameter is different from the second parameter.

18 Claims, 20 Drawing Sheets

(51) Int. Cl.
*A61B 5/11* (2006.01)
*A61G 7/05* (2006.01)
*G06T 7/70* (2017.01)
*G06V 40/10* (2022.01)
*G06V 40/20* (2022.01)
*G08B 21/04* (2006.01)
*H04N 7/18* (2006.01)

(52) U.S. Cl.
CPC .............. *A61G 2203/36* (2013.01); *G06T 2207/30196* (2013.01); *G06T 2207/30232* (2013.01)

(56) References Cited

U.S. PATENT DOCUMENTS

| | | | |
|---|---|---|---|
| 10,786,183 B2 | 9/2020 | Matsunaga et al. | |
| 11,076,778 B1* | 8/2021 | Abbas | A61B 5/0022 |
| 2002/0014951 A1* | 2/2002 | Kramer | G16H 10/60 |
| | | | 340/286.07 |
| 2005/0256390 A1* | 11/2005 | Laux | G01R 33/56383 |
| | | | 600/407 |
| 2008/0172789 A1* | 7/2008 | Elliot | A61G 7/0527 |
| | | | 5/616 |
| 2009/0119843 A1* | 5/2009 | Rodgers | G16Z 99/00 |
| | | | 705/3 |
| 2009/0278934 A1* | 11/2009 | Ecker | G06V 40/25 |
| | | | 348/152 |
| 2010/0212087 A1* | 8/2010 | Leib | A61G 12/00 |
| | | | 5/81.1 R |
| 2014/0104404 A1* | 4/2014 | Locke | G08B 21/02 |
| | | | 348/77 |
| 2014/0371635 A1* | 12/2014 | Shinar | G08B 21/0211 |
| | | | 600/595 |
| 2015/0256665 A1* | 9/2015 | Pera | H04L 12/2816 |
| | | | 455/420 |
| 2016/0314672 A1* | 10/2016 | Wiggermann | A61B 5/1117 |
| 2017/0007480 A1* | 1/2017 | Koch | A61B 5/0077 |
| 2017/0013810 A1* | 1/2017 | Grabell | A01K 61/80 |
| 2018/0145844 A1* | 5/2018 | Pera | H04L 12/2803 |
| 2018/0192779 A1* | 7/2018 | Yan | H04N 21/4131 |
| 2018/0235822 A1* | 8/2018 | Wako | G01L 1/2225 |
| 2018/0373391 A1* | 12/2018 | Cortes | G06F 3/04883 |
| 2019/0008708 A1* | 1/2019 | Moreno | G06F 3/0489 |
| 2019/0121522 A1* | 4/2019 | Davis | G06V 40/28 |
| 2019/0175103 A1* | 6/2019 | Kogure | A61B 5/4809 |
| 2019/0201266 A1* | 7/2019 | Sayadi | A47C 21/003 |
| 2019/0286806 A1* | 9/2019 | Robinson | H04L 63/0853 |
| 2019/0313948 A1 | 10/2019 | Matsunaga et al. | |
| 2020/0060910 A1* | 2/2020 | Lightcap | A61B 5/447 |
| 2020/0205580 A1* | 7/2020 | Sayadi | A47C 27/083 |
| 2021/0022667 A1* | 1/2021 | Sayadi | A61B 5/1126 |
| 2021/0085547 A1* | 3/2021 | Kubota | A61G 7/018 |
| 2021/0106479 A1* | 4/2021 | Zerhusen | A63B 21/4011 |
| 2021/0204720 A1* | 7/2021 | Karschnik | A47C 19/027 |
| 2021/0254850 A1* | 8/2021 | Field | G05D 23/1931 |
| 2021/0315755 A1* | 10/2021 | Matsubayashi | A61G 7/018 |
| 2021/0386319 A1* | 12/2021 | Houbraken | A61B 5/0004 |
| 2022/0024486 A1* | 1/2022 | Scott | G05D 1/0221 |
| 2022/0031196 A1* | 2/2022 | Shinar | G08B 21/0423 |
| 2022/0071512 A1* | 3/2022 | McAnena | A61B 5/6891 |
| 2022/0181019 A1* | 6/2022 | Ukrainksy | G16H 40/20 |
| 2022/0182584 A1* | 6/2022 | Abbas | A61B 5/746 |

FOREIGN PATENT DOCUMENTS

| | | | |
|---|---|---|---|
| JP | 2010-264193 | 11/2010 | |
| JP | 2016-30177 | 3/2016 | |
| JP | 2016-87355 | 5/2016 | |
| JP | 2017-42398 | 3/2017 | |
| JP | 2018-67203 | 4/2018 | |
| JP | 2018-143338 | 9/2018 | |
| JP | 2019-8515 | 1/2019 | |
| JP | 2019-178890 | 10/2019 | |
| WO | 2017/218725 | 12/2017 | |
| WO | WO-2017218725 A1 * | 12/2017 | ........... A61B 5/1115 |

\* cited by examiner

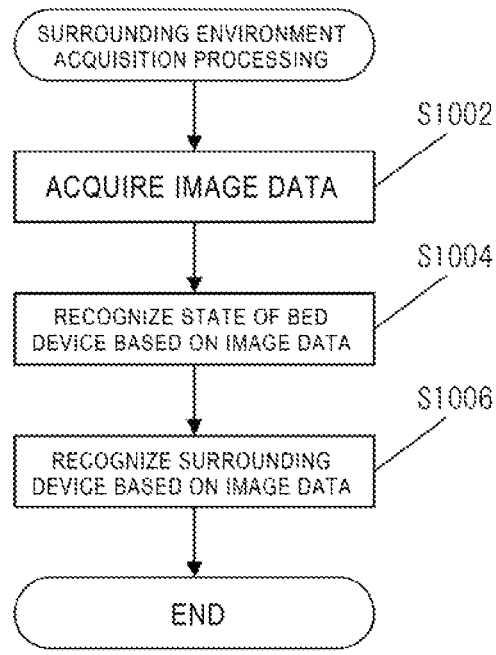

| CAMERA | CAMERA POSITION | CAPTURE RANGE |
|---|---|---|
| CAMERA 20A1 | BED 3A | R112, R114, R116, R118, R120 R202, R204, R206, R208, R210 |
| CAMERA 20A2 | BED 3A | R102, R104, R106, R108, R110 |
| ⋮ | ⋮ | ⋮ |

1250

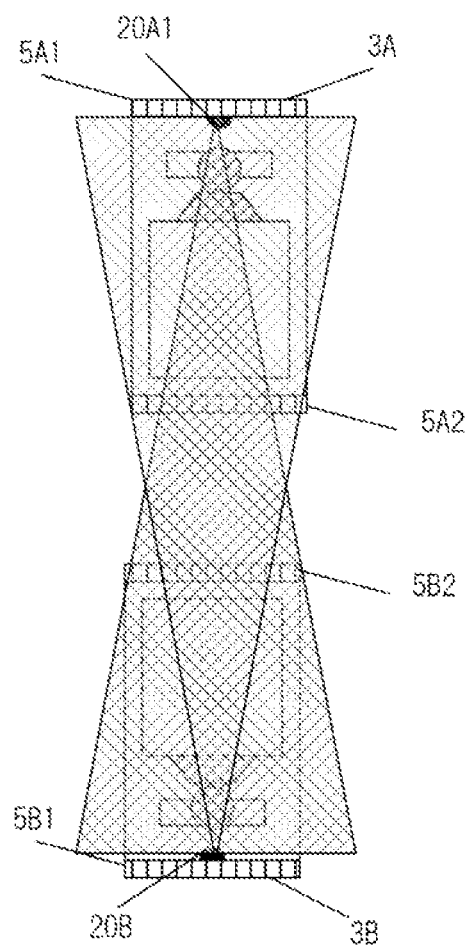

FIG. 20

| SCENE | FEATURE AMOUNT·CAMERA ||||||
|---|---|---|---|---|---|---|
| | SURROUNDING ENVIRONMENT | CAMERA | POSTURE | CAMERA | MOTION | CAMERA |
| INSIDE | SIDE RAIL | b, c, d | CENTER OF GRAVITY | b, c, d | STRETCH OUT HAND OR NOT | b, c, d |
| INSIDE | BOARD INSTALLED OR NOT | b, c, d | POSITION OF HEAD | b, c, d | REMOVE FENCE | b, c, d |
| STANDING | CASTER | a, d | — | — | SHAKE | b, c, d |
| STANDING | EQUIPMENT SURROUNDING BED | a, d | — | — | REMOVE FENCE | b, c, d |
| STANDING | — | — | POSITION OF HAND | b, c, d | WALK WITH SOCKS (SLIPPERS) | a, d |
| SITTING | FLOOR HEIGHT | b, c, d | FOOT ON FLOOR OR NOT | a, d | MOTION OF WEARING FOOTWEAR | a, d |
| SITTING | ASSISTANCE BAR | a, d | SIT DEEPLY OR NOT (POSITIONS OF WAIST AND HIP) | b, c, d | TRY TO PICK UP OBJECT AT DISTANT PLACE OR NOT | d |
| SITTING | EQUIPMENT SURROUNDING BED | b, c, d | — | — | REMOVE FENCE | b, c, d |
| | SENSOR | a, b, c, d | — | — | — | — |

BED SYSTEM

1. FIELD

The present embodiment relates to a bed system and the like.

2. BACKGROUND

There has been proposed a system that provides various kinds of support to a user who uses a bed device. For example, an embodiment is disclosed in which an image capturing a bed and a user is input, and a behavior of departing from the bed and a risk that the user falls are determined based on the image (for example, see JP-A-2019-008515, and JP-A-2018-067203).

BRIEF DESCRIPTION OF THE DRAWINGS

FIGS. 4A and 4B are diagrams for illustrating surrounding environment acquisition processing according to the first embodiment.

FIG. 15 is a diagram for illustrating the operation example according to the fifth embodiment.

FIG. 20 is a diagram for illustrating a modification.

DETAIL DESCRIPTION

Figure 1A:
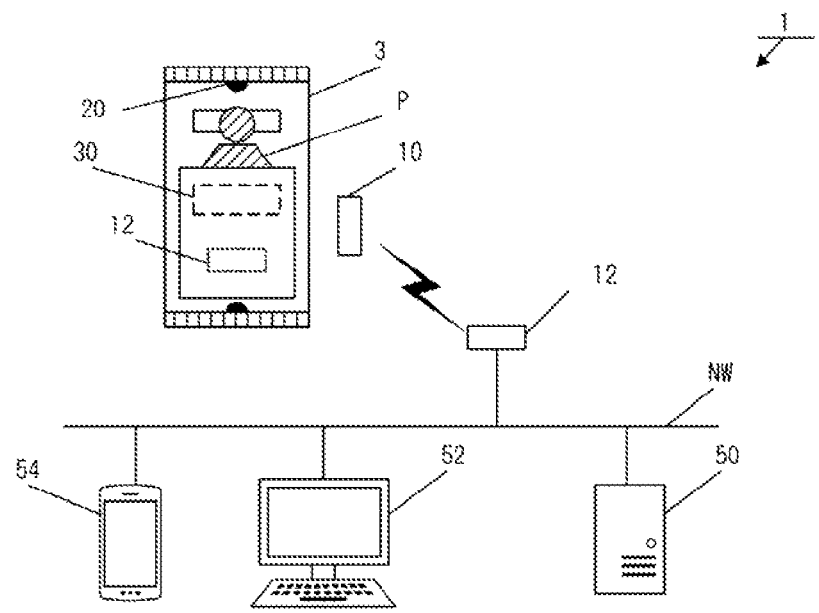
FIGS. 1A to 1C are diagrams illustrating an overall system according to a first embodiment.

One or more embodiments are now described with reference to the drawings, wherein like reference numerals are used to refer to like elements throughout. In the following description, for purposes of explanation, numerous specific details are set forth in order to provide a thorough understanding of the various embodiments. It is evident, however, that the various embodiments can be practiced without these specific details (and without applying to any particular networked environment or standard).

As used in this disclosure, in some embodiments, the terms "component," "system" and the like are intended to refer to, or comprise, a computer-related entity or an entity related to an operational apparatus with one or more specific functionalities, wherein the entity can be either hardware, or a combination of hardware and software in execution.

One or more components may reside within a process and/or thread of execution and a component may be localized on one computer and/or distributed between two or more computers. In addition, these components can execute from various computer readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software application or firmware application executed by a processor, wherein the processor can be internal or external to the apparatus and executes at least a part of the software or firmware application. As yet another example, a component can be an apparatus that provides specific functionality through electronic components without mechanical parts, the electronic components can comprise a processor therein to execute software stored on a non-transitory electronic memory or firmware that confers at least in part the functionality of the electronic components. While various components have been illustrated as separate components, it will be appreciated that multiple components can be implemented as a single component, or a single component can be implemented as multiple components, without departing from example embodiments. Further, the various embodiments can be implemented as a method, apparatus or article of manufacture using standard programming and/or engineering techniques to produce software, firmware, hardware or any combination thereof to control a computer to implement the disclosed subject matter. The term "article of manufacture" as used herein is intended to encompass a computer-readable (or machine-readable) device or computer-readable (or machine-readable) storage/communications media having a computer program stored thereon. For example, computer readable storage media can comprise, but are not limited to, magnetic storage devices (e.g., hard disk, floppy disk, magnetic strips), optical disks (e.g., compact disk (CD), digital versatile disk (DVD)), smart cards, and flash memory devices (e.g., card, stick, key drive). Of course, those skilled in the art will recognize many modifications can be made to this configuration without departing from the scope or spirit of the various embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word example or exemplary is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Embodiments described herein can be exploited in substantially any wireless communication technology, comprising, but not limited to, wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Z-Wave, Zigbee and other 802.XX wireless technologies and/or legacy telecommunication technologies.

In general, one aspect of the present application is a bed system includes, an imaging device, a bed on which the imaging device is to be installed, and a controller configured to process an image acquired by the imaging device to predict a possibility of overturning of a user, in which, when it is determined that a state of the user is a first state, the controller predicts the possibility of overturning of the user based on a first parameter, when it is determined that the state of the user is a second state, the controller predicts the possibility of overturning of the user based on a second parameter, the first state is a state of the user different from the second state, and the first parameter is different from the second parameter.

In general, another aspect of the present application is a bed system includes, a imaging device, a bed on which the imaging device is mounted, and a controller configured to process an image acquired by the imaging device to predict a possibility of overturning of a user, in which, the controller is configured to predict a risk based on a parameter selected based on positions of the bed and the user, and when it is determined that there is a reduction factor based on the image acquired by the imaging device, predict the risk at a level lower than a predicted level.

Hereinafter, one embodiment for implementing a system of the present application will be described with reference to the drawings. Contents of the present application is merely an example of a mode for implementing the present application, and is not limited to the disclosed numerical values and configurations, and includes an equivalent scope that can be conceived by a person skilled in the art.

1. First Embodiment

Various methods are proposed to prevent a user from overturning or falling. For example, a system according to a comparative example analyzes an image in which a bed device and a user are captured. The system according to the comparative example can recognize that the user may depart from the bed or that the user may fall from the bed device by analyzing the image. The system according to the comparative example notifies a health care worker, a staff, an assistant, or the like when there is a high risk of falling of the user.

When a timing of notification to the health care worker, the staff, the assistant, or the like is late, there is a risk that the user falls from the bed device. After the user departs from the bed device, there may be a risk that the user falls due to an environment around the bed device (for example, a wheelchair, a position where shoes are placed, and an arrangement of a side table).

However, when the system according to the comparative example makes a notification at a timing earlier than the timing at which the user departs from the bed device, a notification is excessively (more than necessary) made to the health care worker, the staff, the assistant, or the like, which causes a work burden. A degree of overturning and falling risk varies depending on a physical situation of the user, a difference in the surrounding environment, or the like. Therefore, after the system according to the comparative example sets a notification condition, when the staff or the like is notified based on a uniform criterion according to the setting condition, the staff or the like may not be able to take an appropriate measure according to characteristics of the user or the surrounding environment.

According to a first system of the present embodiment, a system capable of predicting the risk of the user, providing the notification at an appropriate timing, and giving appropriate advice is provided.

The user in the present specification refers to a person who uses the bed device (mattress), and is not limited to a person who receives treatment due to a disease (for example, a patient). A person who receives care in a facility or a person who is on the bed device (for example, a supine person) can be a user even if the person is a healthy person.

In the present specification, the staff or the like includes not only a person who assists the user, such as the health care worker, the staff in the facility, or the family, but also a person related to the user.

In the present specification, a term "obstacle" refers to a reason that causes overturning and falling of the user. For example, obstacles are those such as a table, a pole, and the wheelchair placed near the bed device, and those contained in a living room such as footwear of the user (shoes and sandals) and a curtain. The obstacle may include an event. For example, when a wet floor causes the user to overturn and fall, such an event may also be included in the obstacle.

When the bed device itself is a reason that causes the overturning and falling of the user, the bed device itself may be an obstacle. For example, when a direction of casters of the bed device is not appropriate, or when the casters of the bed device are in an unlocked state, the bed device may be an obstacle. When the direction of the casters is not appropriate, for example, when the user pushes the bed device, the casters may be easily moved.

The overturning and falling in the present specification include overturning and/or falling. For example, the "reason that causes the overturning and falling of the user" includes either or both of the "reason that causes overturning of the user" and the "reason that causes falling of the user".

In the present specification, an image is an image (image data) captured by a camera device, and includes all of a still image, a moving image, and other images captured by the camera device.

1.1 Overall Description

[1.1.1 Description of Overall System]

Figure 1B:
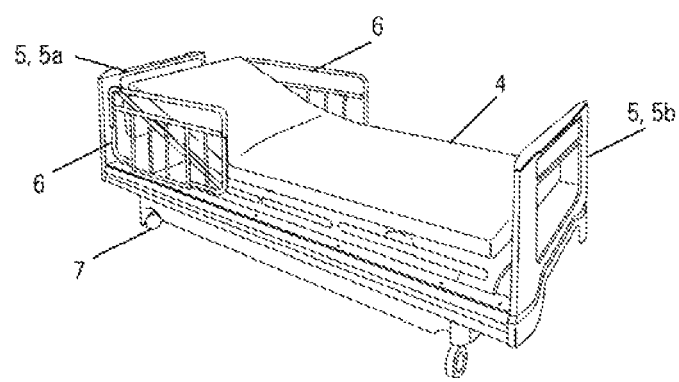
Figure 1C:
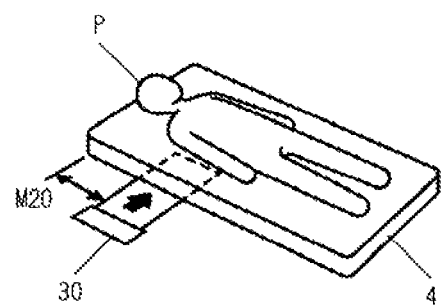

FIG. 1A is an overall view for illustrating an outline of a system 1 according to the present embodiment. FIG. 1B is a diagram for illustrating a configuration of a bed device 3. FIG. 1C is a diagram illustrating an arrangement of a sensor device 30.

As shown in FIG. 1A, the system 1 includes a control device 10, a server device 50, a terminal device 52, and a mobile terminal device 54. The control device 10, the server device 50, the terminal device 52, and the mobile terminal device 54 are communicably connected via a network NW.

The bed device 3 is provided with one or a plurality of movable back sections, seat sections, upper leg sections, lower leg sections, and the like (hereinafter, collectively referred to as "section"), and can perform a back raising motion and a foot raising motion. For example, FIG. 1B shows a state in which the back raising motion is performed by raising the back section. The bed device 3 may place a mattress 4 on the section.

The bed device 3 includes a raising and lowering mechanism, and can change a height (floor height) of the section of the bed device 3. In the present specification, the floor height of the bed device refers to a distance from the floor on which the bed device 3 serving as a criterion is placed to the section. The floor height of the bed device 3, in addition to the distance from the floor to the section, may be a distance from the floor to an upper frame or a distance from the floor to the mattress. The floor height of the bed device may be set such that a criterion position is not the floor but a lower frame.

The bed device 3 can also perform an operation of tilting the entire bed device 3 (tilt operation). The bed device 3 may be a bed device in which any part is not movable.

The bed device 3 can be detachably installed with a board 5. As shown in FIG. 1B, the board can be installed with a head board (board 5a) on a head side, and a foot board (board 5b) on a foot side. The bed device 3 can be detachably installed with a side rail 6. The side rail 6 can be installed on the left and right of the bed device 3. A plurality of the side rails 6 can also be installed in a longitudinal direction of the bed device 3. For example, two side rails 6 may be installed on the head side and the foot side of the bed device 3.

The bed device 3 is movable by using casters 7. The caster 7 includes a lock mechanism. When the bed device 3 is locked by the lock mechanism, movement of the bed device 3 is restricted.

The bed device 3 further includes a camera device 20. The camera device 20 captures an image of a user P, the bed device 3, a state of the surrounding environment, the staff, and the like. A method of installing the camera device 20 will be described later.

Here, the "surrounding environment" refers to an environment of a surrounding range where the bed device 3 is installed (for example, a range included in a predetermined distance from a position where the bed device 3 is installed, a range including a living room or a hospital room where the bed device 3 is present, or a range where the camera device 20 can capture the image). For example, the surrounding environment includes an object arranged around the bed device 3 (for example, a bed head base, and an IV pole), a movable object such as the shoes or the wheelchair, room brightness, and a position of another user, the staff, or the like in a case of a multi-bed room.

In the present specification, the "surrounding" refers to a range (angle of view) that can be captured by the camera device 20. For example, when the camera device 20 can capture an image of a doorway of the living room in which the bed device 3 is installed or an entire range of the living room, the doorway of the living room or the entire range of the living room is also included in the "surrounding".

The sensor device 30 can be placed on the bed device 3. The sensor device 30 is a sensor that detects a body motion of the user who is on the bed device 3. By using the sensor device 30, the control device 10 can acquire a biological information value such as a heartbeat rate and a respiratory rate of the user, and can detect a position, a center of gravity, a posture, and the like of the user.

The sensor device 30 is a sensor capable of detecting a state of the user and a state of the living room and a hospital room. For example, the sensor device 30 may be placed on the mattress 4 on the bed device 3, or may be placed between the section of the bed device 3 and the mattress 4. The position where the sensor device 30 is placed may be a position where the body motion of the user can be detected on the bed device 3. The position where the sensor device 30 is placed is preferably a position corresponding to the back of the user when the user lies down.

For example, as shown in FIG. 1C, the sensor device 30 is placed on or below the mattress 4 placed on the section of the bed device 3. At this time, the sensor device 30 is placed at a position away from a head side end by a distance M20 so as to be located on the back (near the chest) of the user P. For example, M20 is 40 cm.

The sensor device 30 may be implemented by providing a load sensor below the bed device 3 (between the floor and the bed device 3), or may detect the body motion of the user by providing a strain gauge on a frame or a motor supporting the bed.

The sensor device 30 may include other sensors. For example, the sensor device 30 may be an illuminance sensor that detects the brightness of the living room, a position sensor that detects the position of another device, or a sensor that performs face authentication of the user. The sensor device 30 may be an odor sensor that detects excretion of the user. For example, an excretion sensor disclosed in JP-A-2019-178890 (Title of invention: Excretion sensor, Filing date: Mar. 30, 2018) can be used. The patent application is incorporated by reference in its entirety. The sensor device 30 may be any device capable of detecting any information or state.

Equipment is placed as various objects in the living room or the hospital room where the bed device 3 is present. For example, equipment such as a stand (IV stand) to which an infusion or the like can be attached, a pole (IV pole) attached to the bed device 3, the side table, the wheelchair, and a cabinet (bed head base) may be placed. The system 1 may use the camera device 20 to grasp the positions of the equipment and objects, as will be described later. The system 1 may grasp the position and the state of the equipment such as the IV stand, the IV pole, the side table, the wheelchair, and the cabinet by respectively incorporating an IoT unit (including a communication module) therein.

Further, curtains (a curtain around the bed device 3, a curtain attached to a window, and the like) in the living room and the hospital room may be used as the equipment. The system 1 may grasp whether the curtain is open or closed by using the camera device 20 or the IoT unit. The system 1 may use the camera device 20 or the IoT unit to grasp whether the curtain installed surrounding the bed is open or closed. The curtain installed surrounding the bed may be, for example, a curtain for partitioning a space of each patient in a multi-bed room.

The control device 10 is a device that controls the overall system. The control device 10 according to the present embodiment is installed in a tablet device, and may control each device from another device. For example, the control device 10 may display the biological information values such as the heartbeat rate and the respiratory value acquired by the sensor device 30 on a monitor.

The control device 10 may be further connected to another device. For example, the control device 10 may be connected to a bed control device 40 (FIG. 3) that controls the bed device 3. The control device 10 can acquire a state of the bed device 3 and control the bed device 3 (for example, control of back raising/back lowering).

The control device 10 may be constituted integrally with the camera device 20, or may be constituted as a device different from the camera device 20. The control device 10 may be integrated with the bed control device 40 that controls the bed device 3.

The control device 10 may be implemented by a device in another place, or may be provided by installing an application in the terminal device (for example, a smartphone) of the user, the staff or the like. Functions implemented by the control device 10 may be implemented on the server device side.

The control device 10 is constituted to be connectable to the network NW. For example, the control device 10 is connected to an access point 12 via a wireless LAN, and is connected to the network NW. The access point 12 is a base station device of the wireless LAN, and is capable of wireless communication such as IEEE 802.11a/b/g/n. The control device 10 may perform communication using a wired LAN, short-distance wireless communication of Bluetooth (registered trademark), or another communication line such as LTE/5G, instead of the wireless LAN.

The server device 50 is a server that manages information necessary for the system. The server device 50 manages various kinds of information such as information related to a disease of the user, information related to administration, and information related to hospitalization history, and overturn history. The terminal device 52 and the mobile terminal device 54 are devices used by the staff. For example, when there is a risk of overturning and falling, the control device 10 may notify the terminal device 52 or the mobile terminal device 54.

The server device 50 may receive and manage data acquired by the control device 10. For example, the server device 50 may receive and manage an image captured by the camera device 20. The server device 50 is not limited to a server device that manages the present system, and includes a server device that manages a medical system and hospital system, an electronic medical record server device, and a management server device customized by the hospital or the facility.

[1.1.2 Pattern of Camera]

FIGS. 2A to 2D are diagrams for illustrating patterns in which cameras are used. Hereinafter, five patterns will be described. The camera device 20 may be built in or externally attached to the frame of the bed device 3 or the board 5 of the bed device 3 in advance. The camera device 20 may be built in or externally attached to the bed device 3 later.

(Pattern a)

Figure 2A:
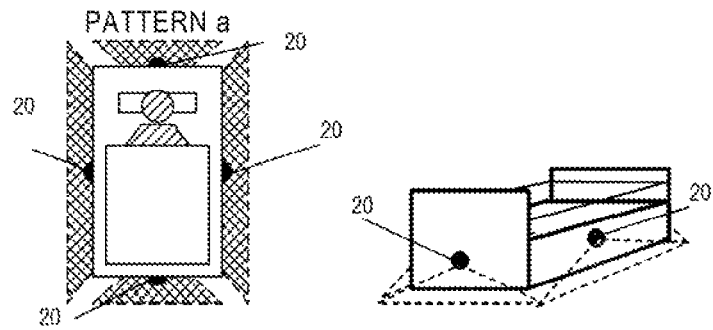
FIGS. 2A to 2D are diagrams for illustrating installation situations of cameras according to the first embodiment.

As illustrated in FIG. 2A, the camera devices 20 are installed surrounding the bed device 3. Specifically, the camera devices 20 are installed in frames on the head side, the foot side, and longitudinal sides (a right hand side of the user and a left hand side of the user) of the bed device 3, the board 5, a fence attached to the bed (for example, an insertion fence, a folding fence, a tracking fence, which is also referred to as the side rail for convenience of description) and an assistance bar, and other dedicated attachment tools using a fence hole or the board. The camera device 20 can capture an outer periphery of the bed device 3, the user, the staff, and the like. For example, the camera device 20 may be a device that can capture an image preferably in a range of 120 to 230 degrees.

Although the camera devices 20 are installed at the center of the frames and the boards 5 in FIG. 2A, the camera device 20 may be installed at any one of four corner locations of the bed device 3, may be installed at each of four corner locations of the bed device 3, or a plurality of camera devices 20, which is two or more on one side, may be installed. The camera device 20 may be installed in combination with one having a different angle of view, or may be installed regardless of the place. A lens of the camera device 20 is installed so as to face the outside of the bed device 3.

(Pattern b)

Figure 2B:
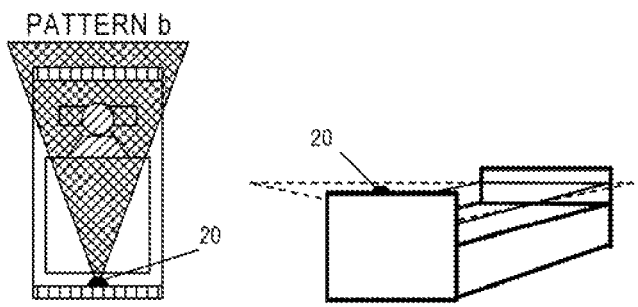

As illustrated in FIG. 2B, the camera device 20 is installed on the board 5. Specifically, the camera device 20 is installed at the center of the foot board on the foot side (board 5*b*) (or the head board on the head side (board 5*a*)) of the bed device 3, so that a full body of the user on the bed device 3 can be captured. The camera device 20 may be a device that can capture an image preferably in a range of 60 to 230 degrees. Two or more camera devices 20 may be installed, or the camera devices 20 having different angles of view may be installed in combination. The camera device 20 may be installed at any place, for example, at the right side or the left side of the foot board (head board), as long as the camera device 20 is installed in a range in which the top of the bed device 3 including the user can be captured. The lens of the camera device 20 is installed so as to face the inside of the bed device 3.

(Pattern c)

Figure 2C:
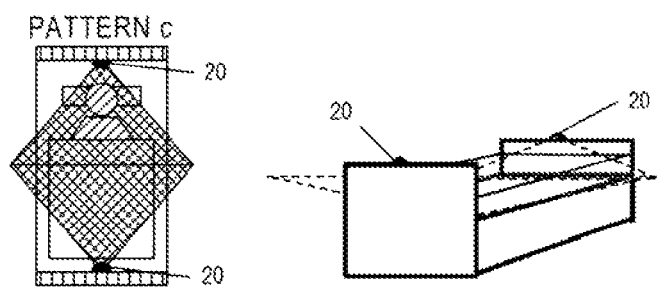

As illustrated in FIG. 2C, the camera devices 20 are installed on the boards 5 on both sides. Specifically, the camera device 20 is installed at the center of the foot board (board 5*b*) and the head board (board 5*a*) of the bed device 3, so that the full body of the user on the bed device 3 can be captured. Other descriptions are the same as those of the second pattern, and detailed descriptions thereof will be omitted.

(Pattern d)

Figure 2D:
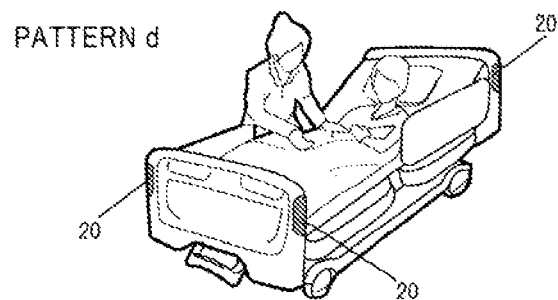

As shown in FIG. 2D, the camera devices 20 are installed at ends of the head board (board 5*a*) and/or the foot board (board 5*b*). For example, the camera device 20 is installed in the vicinity of the end of the foot board or in the vicinity of a grip portion provided above the foot board. In this manner, the camera device 20 is arranged at any place where the user and the periphery of the bed device 3 can be captured.

In this way, the camera device 20 is provided so as to correspond to one bed device 3, instead of a camera device that is present in a room in advance. Accordingly, the camera device 20 does not need to perform calibration on the bed device 3, the surrounding environment, or the like, and convenience of the user, the staff, or the like is improved. Even when the user of the bed device 3 is changed or the living room in which the bed device 3 is arranged is changed, since the bed device 3 and the camera device 20 correspond to each other, it is not necessary to change the data stored in the system, and the convenience of the user, the staff, and the like is improved. For example, since it is not necessary to perform the calibration, even when the staff or the like forgets to perform the calibration, it is possible to appropriately use the camera.

(Pattern e)

In the above patterns, the camera device 20 is installed in the bed device 3 as an example. However, for example, a camera device 20 already installed in the living room or a camera device 20 installed in the equipment can be used. Specifically, when a monitoring camera or the like is already installed, an image thereof may be used. In this case, a camera device 20 at a position where the user P on the bed device 3 is within the angle of view is used.

The patterns a to e described above can be installed in combination as necessary. For example, an installation pattern can be a combination of the pattern a and the pattern c, or a combination of the pattern c and the pattern d.

As for the pattern using the camera, the camera device 20 may be installed at each position later (installed afterwards), or may be installed in advance (installed in an initial state). It is also assumed that the pattern using the camera includes selecting and using a camera from the already set cameras. For example, the cameras are installed in advance at the locations of FIGS. 2A, 2C, and 2D. At this time, in the case of the pattern c, the system 1 does not use the cameras shown in FIG. 2A or 2D, but uses the cameras installed in FIG. 2C (board 5).

[1.1.3 Acquirable Data By Camera Device]

The control device 10 can acquire the following data by analyzing the image captured by the camera device 20. Hereinafter, an overview of acquirable data will be described.

(1) Behavior of User

For example, as a behavior of the user, it is possible to acquire an action of taking a meal (including a meal amount), water or the like (including a water intake amount), the number of times of rolling over, apnea, a frequency of use of a portable toilet, presence or absence of a prohibited behavior, an abnormal behavior, whether to take medicine, and presence or absence of a scratching behavior.

(2) State of User

For example, it is possible to acquire, as a state of the user, a change in a physical condition of the user, a facial expression of the user, an emotion of the user, concussion of the user, bleeding of the user, biological information of the user, a sleeping posture of the user, bed-departure and on-bed of the user (including duration of departing from the bed or while on the bed), a situation when the user falls, and the like.

(3) Detection of Person

For example, it is possible to detect and recognize a user, a staff in the hospital and the facility, a family member, others, and a third party in the capturing range.

(4) Other Information

For example, it is possible to recognize medical record information, a remaining amount of infusion used by the user, a remaining amount of consumables used by the user or in the living room, presence or absence of bed wiping, a position of an auxiliary tool, a state of an object or an obstacle around the bed device 3 or below the bed device 3, a state of a floor (whether or not the floor is wet), a state of an article (whether or not it is appropriate for the situation where the object is placed, whether or not the object is broken, or the like), a position of wiring such as a cable, a behavior of the staff such as the nurse or the family member (treatment performed by the staff or the like, forgetting a power supply of the living room or the device), a time point when the staff or the like visits the user, an unvisited duration time, a position or the presence or absence of use of equipment in the living room, a scene of the entire living room, presence or absence of violence against the user and the staff, presence or absence of theft in the living room, a disaster such as leakage of water or fire (including information on an occurrence place of a disaster or the like), and the like.

The control device 10 may acquire data to be acquired from the captured image by analyzing and recognizing the image as described later, or may acquire the data by artificial intelligence (AI) based on the captured image.

For example, the system 1 (the control device 10) accumulates, in a database, images captured including the inside of the living room including the bed device 3 and the user. At this time, the control device 10 causes the neural network to learn a relationship between the captured images and information corresponding to the behavior of the user, the state of the user, the person to be detected, and other images by deep learning.

Then, the control device 10 can acquire necessary data to be described later by using the learned neural network based on the captured image including the inside of the living room including the bed device 3 and the user.

[1.1.4 Input Parameters and Output Parameters]

The control device 10 can obtain an output by inputting some parameters to a learned model or a neural network subjected to machine learning. Hereinafter, parameters input by the control device 10 and parameters output by the control device 10 will be described based on some situations.

(1) First Situation

The control device 10 recognizes how much water the user takes in while on the bed based on the image captured by the camera device 20, predicts bed-departure based on a recognition result, and notifies the staff or the like of a recommendation of "please guide the user to the toilet".

In this case, the control device 10 inputs "water intake amount" and "duration on bed" as input parameters. The control device 10 outputs "bed-departure prediction" and "recommendation notification" as output parameters.

(2) Second Situation

The control device 10 notifies a priority and a necessary preparation item (article) of a patient who is the user to be circulated by the staff based on a content of treatment previously performed by the staff (for example, the medical treatment performed by the staff on the user) and an elapsed time (unvisited duration) thereafter.

In this case, the control device 10 inputs "previously performed treatment" and "unvisited duration" as the input parameters. The control device 10 outputs "circulation priority notification" and "necessary preparation item (article) during visiting" as the output parameters.

(3) Third Situation

When a fire (camera) or an earthquake (vibration) occurs, the control device 10 notifies the patient who is the user or the staff in the vicinity of the fire or the earthquake or the user or the staff who is away from the fire or the earthquake of an alert. The control device 10 notifies a different type of alert according to a notification destination. For example, the user or the staff in the vicinity of an occurrence place of a disaster is notified of an alert for evacuation. The user or the staff in a place away from the occurrence place is notified of an alert for standby.

The control device 10 inputs "fire and earthquake", "occurrence place", and "whether or not the user is on the bed" as the input parameters. The control device 10 outputs "disaster alarm" as the output parameter (4) Fourth Situation The control device 10 issues a notification for preventing the staff from forgetting the treatment. For example, the control device 10 issues a notification for preventing a case where a plurality of medicines have to be administered to the user according to a medical record but a part of the medicines are not administered. The treatment of the staff may include not only the treatment for the user (for example, confirmation of infusion or wiping) but also the treatment of the staff themselves (for example, sanitizing hands of the staff).

The control device 10 inputs "staff treatment" and "medical record information" as the input parameters. The control device 10 outputs a "treatment forgetting alert" as the output parameter.

(5) Fifth Situation

The control device 10 issues the notification according to the state and the motion of the user. For example, when the user is a paralyzed patient, the control device 10 reads from the motion and notifies what the user cannot do even though he/she wants to (request).

The control device 10 inputs "posture", "motion", and "medical record information" as the input parameters. The control device 10 outputs "request estimation (notification)" as the output parameter.

(6) Sixth Situation

The control device 10 performs treatment necessity determination based on an overturn process of the patient (for example, which part is hit with what degree of strength).

The control device 10 inputs a "hit part", an "overturn speed", and an "impact sound" as the input parameters. The control device 10 outputs "treatment necessity determination" as the output parameter.

(7) Seventh Situation

The control device 10 recommends changes in the surrounding equipment (environment) in accordance with changes in sensor setting. For example, when a setting of a bed-departure sensor is changed from "getting up" to a "sitting position" (that is, when it becomes possible to stand up), the control device 10 recommends not the currently used insertion fence but the assistance bar.

The control device 10 inputs "sensor setting change (operation of a nurse)", "surrounding equipment", and the "medical record information" as the input parameters. The control device 10 outputs "equipment and layout change recommendation" as the output parameter.

(8) Eighth Situation

The control device 10 detects the motion of the user. When there is a change in the physical information described in the medical record information (for example, a decrease/increase of the ADL), the control device 10 recommends the change in the surrounding equipment (environment) in accordance with the change.

The control device 10 inputs the "motion", the "surrounding equipment", and the "medical record information" as the input parameters. The control device 10 outputs the "equipment and layout change recommendation" as the output parameter.

(9) Ninth Situation

The control device 10 notifies the staff when the camera captures an event in which an object falls from a position where it is supposed to be present and detects the motion of the user trying to pick up the object.

The control device 10 inputs "dropping of object", "hand stretching out action", and the "medical record information" as the input parameters. The control device 10 outputs a "fallen object notification (overturn prevention)" as the output parameter.

[1.2 Description of Functional Configuration and Processing]

Figure 3:
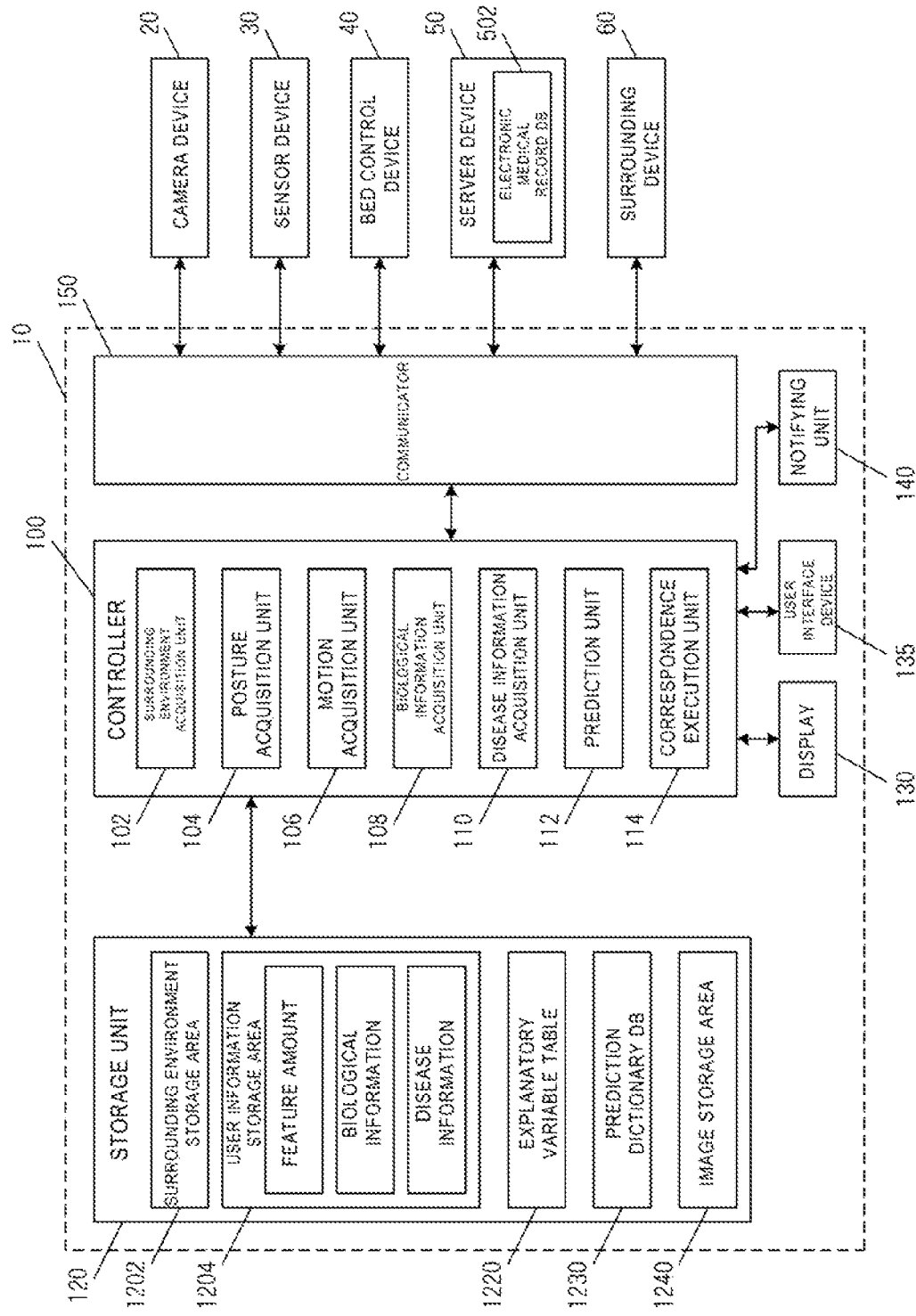
FIG. 3 is a diagram for illustrating a functional configuration according to the first embodiment.

Next, in the system 1 according to the present embodiment, a functional configuration centered on the control device 10 will be described with reference to FIG. 3.

[1.2.1 Controller and Storage Unit]

The control device 10 includes a controller 100, a storage unit 120, a display 130, a user interface device 135, a notifying unit 140, and a communicator 150. The communicator 150 can be connected to the camera device 20, the sensor device 30, the bed control device 40, the server device 50, and a peripheral device 60.

The controller 100 controls the overall control device 10. The controller 100 is one or a plurality of calculation units (for example, central processing units (CPUs)) that implement various functions by reading and executing various programs stored in the storage unit 120.

The controller 100 functions as an acquisition unit including a surrounding environment acquisition unit 102, a posture acquisition unit 104, a motion acquisition unit 106, a biological information acquisition unit 108, and a disease information acquisition unit 110 by reading and executing the programs stored in the storage unit 120. The controller 100 functions as a prediction unit 112 and a correspondence execution unit 114.

The storage unit 120 stores various programs and various kinds of data necessary for the operation of the control device 10. The storage unit 120 includes, for example, a solid state drive (SSD) which is a semiconductor memory, and a hard disk drive (HDD).

The storage unit 120 includes a surrounding environment storage area 1202, a user information storage area 1204 for storing user information, and an image storage area 1240, and stores an explanatory variable table 1220 and a prediction dictionary DB 1230.

Hereinafter, functions implemented by the controller 100 will be described. Here, when the controller 100 functions as the acquisition unit, each acquisition unit outputs a feature amount as a parameter usable by the prediction unit 112 based on a predetermined input value. The acquisition unit can output one or a plurality of feature amounts described below in combination.

(1) Surrounding Environment Acquisition Unit (First Acquisition Unit)

The surrounding environment acquisition unit 102 acquires an obstacle from the equipment included in the image, and acquires the surrounding environment of the bed device 3 such as the surrounding brightness, based on the image captured by the camera device 20. The surrounding environment acquisition unit 102 outputs and stores the feature amount based on the acquired surrounding environment in the surrounding environment storage area 1202.

Surrounding environment acquisition processing executed by the surrounding environment acquisition unit 102 will be described with reference to FIG. 4A. First, the surrounding environment acquisition unit 102 acquires an image from the camera device 20 (step S1002). Specifically, when the control device 10 periodically acquires the image from the camera device 20, the controller 100 stores the received image in the image storage area 1240. In this case, the surrounding environment acquisition unit 102 reads and acquires the image from the image storage area 1240 in step S1002. Without being limited thereto, for example, when the control device 10 controls the camera device 20 to receive the image, the surrounding environment acquisition unit 102 may directly acquire the image from the camera device 20 in step S1002.

It is preferable that the surrounding environment acquisition unit 102 uses the camera device 20 arranged in the pattern a and the pattern d. When the surrounding environment acquisition unit 102 acquires the state of the bed device 3 (the state of back raising or the like), the surrounding environment acquisition unit 102 may use the camera device 20 arranged in the pattern b or the pattern c.

The surrounding environment acquisition unit 102 recognizes the state of the bed device 3 based on the image (step S1004). Here, the state of the bed device 3 means a situation of a movable portion when at least a part of the bed device 3 is movable.

The surrounding environment acquisition unit 102 analyzes the image and recognizes items such as the height (floor height) of the section of the bed device 3, a back raising angle, an upper leg raising angle, an inclination angle (tilt angle), and whether or not the back section and the upper leg section operate in conjunction with each other as the state of the bed device 3. For example, the surrounding environment acquisition unit 102 outputs "20 cm" as the floor height of the bed device 3, "20 degrees" as the back raising angle, and "10 degrees" as the upper leg raising angle as one of the feature amounts.

The surrounding environment acquisition unit 102 analyzes the image to recognize the obstacle (step S1006). When the surrounding environment acquisition unit 102 recognizes the obstacle as the surrounding environment, the surrounding environment acquisition unit 102 recognizes, as the obstacle, the equipment or the object that may cause overturning and falling among the equipment or the object included in the image. Then, the surrounding environment acquisition unit 102 recognizes a type, a position, and a direction of the obstacle, whether or not the obstacle is on a route, a size, a shape, presence or absence of the motion, a distance from the bed device 3, and the like as necessary. The surrounding environment acquisition unit 102 outputs information related to the recognized obstacle as one of the feature amounts.

For example, the surrounding environment acquisition unit 102 outputs as the feature amounts that the type of the obstacle is the "wheelchair", the size thereof is "56 cm×100 cm" and the position is at "30 cm on the right side of the bed device 3".

The surrounding environment acquisition unit 102 may recognize the direction of the casters 7 of the bed device 3, a lock state, presence or absence of the side rail (presence or absence of installation, presence or absence of use), and the presence or absence of the assistance bar (presence or absence of installation, presence or absence of use) as the state of the bed device 3 or the obstacle. The surrounding environment acquisition unit 102 outputs a recognition result as the feature amount.

Although the surrounding environment acquisition unit 102 acquires the surrounding environment by recognizing the image of the camera device 20 in the above description, the surrounding environment acquisition unit 102 may acquire the surrounding environment from other than the image. For example, the surrounding environment acquisition unit 102 may directly acquire the back raising angle, the upper leg raising angle, the floor height, and the like of the bed device 3 from the bed control device 40 and output the acquired information as the feature amount. The surrounding environment acquisition unit 102 may acquire the type, the position, the size, and the like of the obstacle by communicating with the peripheral device 60 provided in the obstacle.

The surrounding environment acquisition unit 102 may selectively execute steps S1004 to S1006 in FIG. 4A. For example, only one of the three steps may be executed, or two of the three steps may be executed. The surrounding environment acquisition unit 102 may execute the steps in any combination.

FIG. 4B is a diagram illustrating an example of a first feature amount related to the surrounding environment stored in the surrounding environment storage area 1202. For example, the surrounding environment storage area 1202 stores the feature amount of the state of the bed device 3 and the feature amount based on the obstacle.

The surrounding environment storage area 1202 is capable of storing, as feature amounts related to the bed device 3, the floor height, the back raising angle, the upper leg raising angle, a foot raising angle, the inclination angle (tilt angle), and whether or not the back section and the upper leg section operate in conjunction with each other.

When recognizing the state of the bed device 3, the surrounding environment acquisition unit 102 may also recognize the state of a thing that is used in association with the bed device 3 (for example, an air mat). The surrounding environment storage area 1202 may store the state of the operation of the bed device 3 as the feature amount. For example, when the back section and the upper leg section of the bed device 3 are in conjunction, the surrounding environment storage area 1202 may store a flag "1" as the feature amount. When a rolling operation is performed in the bed device 3, the flag "1" may be stored as the feature amount.

The surrounding environment storage area 1202 may store equipment or the like mounted on the bed device 3. For example, the presence and absence of the board 5, the presence and absence of the side rail 6, and the state of the casters 7 may be stored. The surrounding environment storage area 1202 may store the presence or absence of the head board/foot board as the board 5, and a place where the side rail 6 is mounted (for example, the right side, the left side, the upper side (head side), and the lower side).

The surrounding environment storage area 1202 stores the type of the obstacle, the position of the obstacle, and the like as the feature amount related to the obstacle. The surrounding environment storage area 1202 may store the position of the obstacle in terms of the distance from the bed device 3 or the camera device 20 as the feature amount, or may store relative position coordinates (for example, XYZ coordinates in which the living room is a virtual space). The surrounding environment storage area 1202 may store the feature amount corresponding to the "assistance bar", the "table", or the like, which is the type of the obstacle, or may store the size of the obstacle itself (for example, width x cm, length y cm, and height z cm) as the feature amount.

The surrounding environment storage area 1202 may store the feature amount in the user information storage area 1204 in association with an ID of the user or a time point.

(2) Posture Acquisition Unit (Second Acquisition Unit)

The posture acquisition unit 104 acquires the posture of the user from the image captured by the camera device 20, and outputs the feature amount. Here, the posture of the user refers to away of holding the body of the user, and is estimated based on the image. The posture acquisition unit 104 may acquire not only the way of holding the body of the user but also, for example, the position of the user (whether or not the user departs from the bed) and the place (whether or not the user is at the sitting position) as the posture to be estimated. "Acquiring the posture" refers to specifying a posture based on feature points of a user as described later, and also includes a concept of estimating the posture of the user based on a part of the feature points.

The posture acquisition unit 104 may store the acquired posture of the user in the user information storage area 1204 in association with the user together with an acquisition time point.

Then, the posture acquisition unit 104 outputs the feature amount based on the acquired posture. The feature amount may be a feature amount for each posture such as "1" in the case of the sitting position, "2" in the case of a supine position, and "0" in other cases, or may be an angle of the direction of the user (for example, "10 degrees to the right"), a position of the head (for example, "+5 degrees" with respect to a vertical direction), or a way of holding the body of the user (for example, "angle of raising the right hand"). The posture acquisition unit 104 may output "1" as the feature amount in a case where all postures or the way of holding the body is set as an attribute.

The posture acquisition unit 104 stores a second feature amount based on the acquired posture of the user in the user information storage area 1204 in association with each user.

Figure 5A:
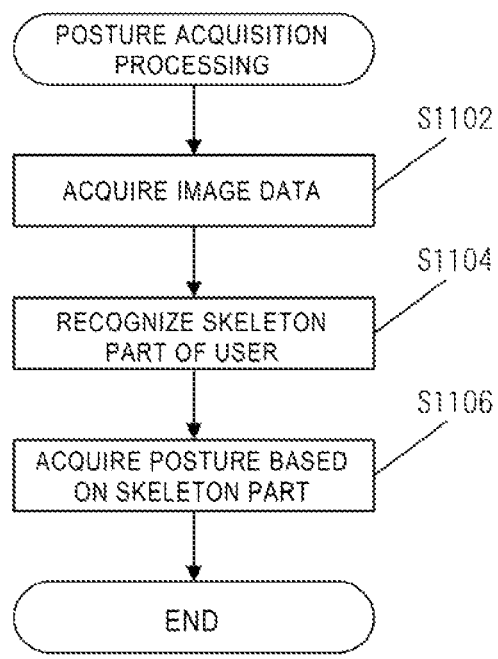
FIGS. 5A and 5B are diagrams for illustrating posture acquisition processing according to the first embodiment.

Posture acquisition processing executed by the posture acquisition unit 104 will be described with reference to FIG. 5A. First, the posture acquisition unit 104 acquires an image (step S1102). The posture acquisition unit 104 can acquire the image by using the same method as that used by the surrounding environment acquisition unit 102 to acquire the image.

The posture acquisition unit 104 recognizes a skeleton part of the user as the feature point based on the acquired image (step S1104). For example, the posture acquisition unit 104 recognizes a position of a shoulder, a position of a face, a position of a hand, and a position of a foot of the user, and also recognizes a position of a joint such as an upper leg joint or an elbow joint by pattern image recognition.

Figure 5B:
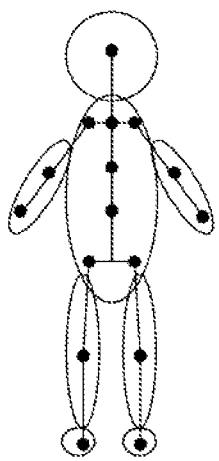

FIG. 5B is a diagram schematically illustrating the skeleton part of the user. For example, the posture acquisition unit 104 recognizes the captured skeleton part of the user by pattern image analysis, and recognizes each feature point of the user. Then, the posture acquisition unit 104 can recognize the skeleton of the user by detecting a line connecting the recognized feature points of a human body.

The posture acquisition unit 104 acquires the size of the user, the posture such as the direction of the body of the user (including the direction of the body, the direction of the face, and the direction of a line of sight), and the way of holding the body of the user by using the feature points (step S1106). In the acquisition of the posture of the user, for example, the posture may be acquired by performing coordinate regression analysis on the feature points, or the posture may be acquired using a result of machine learning. Then, the posture acquisition unit 104 outputs the second feature amount based on the acquired posture.

Although the posture acquisition unit 104 is described as acquiring the posture of the user by recognizing the feature points based on the captured image, another method may be used. For example, the posture of the user may be directly acquired from the image by using a neural network.

A person or a posture of the person in the image may be recognized from the image by an Instance Segmentation method. Specifically, the posture acquisition unit 104 recognizes an area of the object included in the image (the person, the bed device 3, or the like) or an area in which a part of the person is present as the object. That is, the posture acquisition unit 104 may acquire the posture of the user by recognizing an area including the person or recognizing an area of the hand, the foot, or the like of the person.

A method of acquiring the posture or the like of the user other than the above may be used. For example, a method for detecting a state of a user disclosed in JP-A-2009-118980 (Title of invention: State detection system for user in bed, Filing date: Nov. 13, 2007), and a method for detecting a position of a user disclosed in JP-A-2008-206869 (Title of invention: Bed device, Filing date: Feb. 27, 2007) can be incorporated. The patent application is incorporated by reference in its entirety.

In the above description, the posture acquisition unit 104 outputs the feature amount based on the posture of the user based on the image captured by the camera device 20. However, in addition to that, the posture acquisition unit 104 may acquire the posture of the user and output the feature amount by using, for example, the sensor device 30.

The posture acquisition unit 104 may acquire a facial expression from the face of the user by analyzing the image. When the facial expression is acquired, the posture acquisition unit 104 outputs the feature amount based on the facial expression.

(3) Motion Acquisition Unit (Third Acquisition Unit)

The motion acquisition unit 106 acquires the motion of the user based on information (sensor information) acquired by the camera device 20 or the sensor device 30, and outputs the feature amount based on the motion of the user. Here, the motion of the user refers to a movement of the body of the user. Examples of the motion of the user include a movement amount of the user, a movement of the hand or foot of the user, a position of a center of gravity (including a movement of the position of the center of gravity), wobbling, gait, behavior, and rolling over. The motion of the user includes not only the motion such as standing up but also a speed of standing up, a walking speed, a direction of a direction change, and a time related to the direction change. The motion acquisition unit 106 may store the acquired motion of the user in the user information storage area 1204 in time series for each user.

Figure 6:
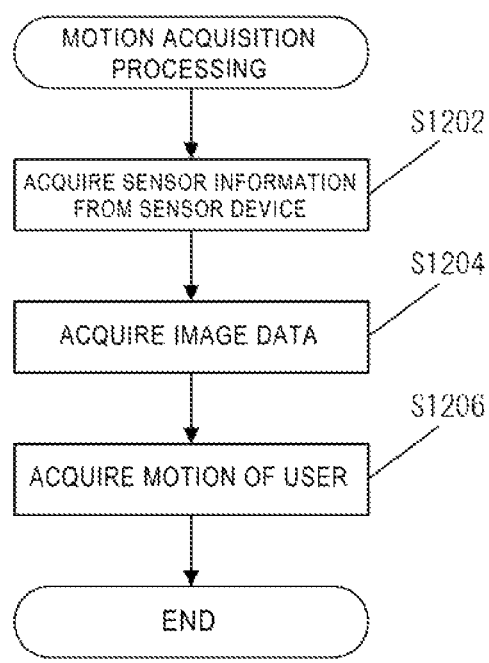
FIG. 6 is a diagram for illustrating motion acquisition processing according to the first embodiment.

Motion acquisition processing executed by the motion acquisition unit 106 will be described with reference to FIG. 6. First, the motion acquisition unit 106 acquires the sensor information from the camera device 20 or the sensor device 30 (steps S1202 and S1204). The sensor information output by the sensor device 30 is, for example, vibration data. The motion acquisition unit 106 can acquire the motion of the user by analyzing the vibration data or the image (step S1206).

Here, the information acquired by the motion acquisition unit 106 from the camera device 20 is an image. The motion acquisition unit 106 estimates the posture of the user in time series based on the image, and acquires the motion of the user such as the position of the center of gravity, the wobbling, the gait, and the behavior of the user. The information to be acquired by the motion acquisition unit 106 from the sensor device 30 in order to acquire the motion of the user is, for example, a load change amount on the bed, data on center-of-gravity, vibration data of air pressure (including body motion data, heartbeat data, and respiratory data which are vital data of the user). That is, the motion acquisition unit 106 can acquire the motion of the user based on the information acquired from the sensor device 30.

Then, the motion acquisition unit 106 outputs a feature amount based on the acquired motion as the feature amount, and stores the feature amount in the user information storage area 1204. Here, what is stored as the feature amount based on the motion is, for example, as follows.

- When it is acquired that the body motion of the user is large, "1" is stored as the feature amount.
- When it is acquired that the user (or a part of the body of the user) moves a predetermined distance or more, "1" is stored as the feature amount.
- When it is acquired that the load change is equal to or greater than a threshold value, "1" is stored as the feature amount. A numerical value of the load change is stored as the feature amount.

The number of times of rolling over is stored as a feature amount.

When there is no change in the motion of the user, the motion acquisition unit 106 may store the fact that there is no change in the motion of the user in the user information storage area 1204 as the feature amount. That is, the motion acquisition unit 106 may acquire the motion of the user periodically (for example, every 1 second, 5 seconds, 1 minute, or 5 minutes) and store a third feature amount based on the motion in the user information storage area 1204.

(4) Biological Information Acquisition Unit (Fourth Acquisition Unit)

The biological information acquisition unit 108 acquires biological information based on the information acquired by the sensor device 30. For example, the biological information acquisition unit 108 calculates a respiratory waveform or a heartbeat waveform based on the body motion received from the sensor device 30 by executing biological information acquisition processing. Then, the biological information acquisition unit 108 acquires a respiratory rate from the calculated respiratory waveform and a heartbeat rate from the calculated heartbeat waveform as values of the biological information. The biological information acquisition unit 108 calculates a fourth feature amount based on the biological information value and outputs the fourth feature amount.

As a method of acquiring the biological information such as the respiratory rate and the heartbeat rate, for example, a method disclosed in JP-A-2016-30177 (Title of invention: Respiratory disorder determination device, respiratory disorder determination method and program, Filing date: Jul. 30, 2014) can be incorporated. Other known techniques may be used.

In addition to the respiratory rate and the heartbeat rate, the biological information acquisition unit 108 can also acquire values of the biological information such as body temperature, blood pressure, and transdermal arterial oxygen saturation (SpO2). The biological information acquisition unit 108 may acquire the biological information (for example, a pulse value or the respiratory rate) that can be continuously acquired by the sensor device 30, or may acquire any of the biological information that can be discretely (in a spot manner) acquired by an external device or the like, such as the blood pressure measured by a sphygmomanometer or the body temperature measured by a thermometer.

The biological information acquisition unit 108 may store the biological information value as it is in the user information storage area 1204 for each user as the feature amount. The biological information acquisition unit 108 may acquire that the biological information value is, for example, a normal level, a caution level, or a warning level, and may output the feature amount according to the level.

The biological information acquisition unit 108 may acquire information related to the user that can be acquired based on the biological information. For example, the biological information acquisition unit 108 may acquire a sleep state or an awake state of the user, and may further acquire REM sleep and non-REM sleep as the sleep state. The biological information acquisition unit 108 may output "1" as the feature amount of sleep when the user is in the sleep state and "0" as the feature amount of sleep when the user is in the awake state.

As a method of determining the sleep state of the users, for example, methods disclosed in JP-A-2010-264193 (Title of invention: Sleep state determination device, program, and sleep state determination system, Filing date: May 18, 2009) and JP-A-2016-87355 (Title of invention: Sleep state determination device, sleep state determination method, and program, Filing date: Nov. 11, 2014) can be incorporated. The patent application is incorporated by reference in its entirety. Other known methods may be used to acquire the sleep/awake state of the user.

The biological information acquisition unit 108 may acquire the biological information of the user from the camera device 20. As the biological information that can be acquired by the biological information acquisition unit 108, for example, the facial expression or the line of sight of the user, and the body motion (for example, restless legs syndrome during sleep, or the like) can be acquired. The biological information acquisition unit 108 can detect body motion and acquire respiration and heartbeat by performing image analysis on the image. The biological information acquisition unit 108 can acquire the body temperature by using a thermal infrared camera device as the camera device 20.

(5) Disease Information Acquisition Unit (Fifth Acquisition Unit)

The disease information acquisition unit 110 acquires information related to a disease of the user (disease information). For example, when the disease information acquisition unit 110 executes disease information acquisition processing, the disease information acquisition unit 110 is connected to the server device 50 and accesses an electronic medical record DB 502. Then, the disease information acquisition unit 110 acquires the information on the disease of the user. Here, the disease information includes, in a broad sense, information related to the disease of the user, and includes not only information related to a simple disease state, but also information related to administration, information related to operation, information related to surgery, information such as hospitalization history, information such as having paralysis of hands and feet, precautions in meals, whether or not an auxiliary tool is used, and precautions related to the user.

The disease information acquisition unit 110 stores the feature amount based on the disease information in the user information storage area 1204. The feature amount acquired by the disease information acquisition unit 110 may be, for example, a feature amount based on a disease history, a medical history, or an admission history. The disease information may include an overturn history. The staff or the like may input the overturn history, or the system may detect the number of times the user overturns and automatically update the overturn history. The feature amount acquired by the disease information acquisition unit 110 may be a feature amount based on medicine taking information, health checkup information, records of various kinds of assessment (including overturn assessment), and the like of the user.

The disease information acquisition unit 110 may output the number of hospitalization days as a fifth feature amount. The disease information acquisition unit 110 may output "1" as the fifth feature amount when the disease corresponds to a specific disease, or may calculate and output the fifth feature amount based on a blood pressure value or a blood glucose value of the user.

(6) Prediction Unit

The prediction unit 112 uses the prediction dictionary DB 1230, which is a prediction model, to predict the risk of overturning and falling. The prediction unit 112 may predict a probability or a future time point at which overturning and falling may occur as the possibility of the overturning and falling. The prediction dictionary DB 1230 is dictionary data of a learned model generated by any one of the machine learning methods.

The prediction unit 112 inputs the above-described feature amount to an artificial intelligence program as an explanatory variable. The artificial intelligence program uses the prediction dictionary DB 1230 to output, as an objective variable, the risk (possibility) of the user overturning and falling.

In the example described above, although the prediction unit 112 outputs the risk (possibility) of the user overturning and falling based on a plurality of feature amounts, the present embodiment is not limited thereto. The prediction unit 112 may predict the possibility of the user overturning and falling based on the image captured by the camera device 20 without obtaining the plurality of feature amounts. For example, a necessary feature amount may be acquired from the image captured by the camera device 20 using a learning model created using a convolutional neural network (CNN). The prediction unit 112 may output the possibility of the overturning and falling using the learning model created from the image captured by the camera device 20 using the convolutional neural network (CNN) or a recurrent neural network (RNN).

As the risk of overturning and falling, for example, the probability of the risk that the user overturns or falls and/or a time point at which the user overturns or falls (predicted future time point) is output.

The prediction unit 112 may output the risk of overturning and falling as a level instead of the probability of the risk as the possibility of overturning and falling. For example, the prediction unit 112 may output that the risk is high when the probability is equal to or greater than a threshold value (for example, 50% or more), and that the risk is low when the probability is less than the threshold (for example, less than 50%). The prediction unit 112 may output a plurality of levels such as an overturning and falling risk being "high", "slightly high", "slightly low", and "low" by providing a plurality of threshold values.

The threshold value for determining the risk by the prediction unit 112 may be set by the staff or the like in common, or may be set by the staff or the like for each user. The controller 100 may appropriately change the value according to the state of the user.

It is assumed that the present specification includes the case that the prediction unit 112 outputs the risk of overturning and falling with the probability and the case that the prediction unit 112 outputs the risk with the level. Even when it is described that the prediction unit 112 outputs the risk of overturning and falling with the probability, the prediction unit 112 may output the risk with the level. Even when it is described that the prediction unit 112 outputs the risk of overturning and falling with the level, the prediction unit 112 may output the risk with the probability.

The prediction unit 112 can output a time point or a time when the risk of overturning and falling is high. For example, the prediction unit 112 can output that the risk of overturning and falling is high at 6 o'clock in the morning, and can output that the risk of overturning and falling is high after 5 minutes or 15 seconds from the current time point.

Hereinafter, an operation of prediction processing executed by the prediction unit 112 will be described with reference to FIG. 7.

First, the prediction unit 112 acquires the overturn assessment from the disease information acquisition unit 110 (step S1300). The overturn assessment includes, for example, (1) an age of the user, (2) a past medical history of the user, (3) a degree of physical functional disorder of the user, (4) a degree of mental functional disorder of the user, (5) an activity situation of the user, (6) information on drugs administered to the user, (7) an excretion situation of the user, (8) a type of a sensor used by the user and setting information thereof, and (9) a type of a fence used by the user and an installation number of the fence.

The prediction unit 112 evaluates a degree of potential overturning and falling risk for each user based on the overturn assessment (step S1301).

The prediction unit 112 predicts the overturning and falling risk of the user based on the potential overturning and falling risk for each user and the information acquired from the camera device 20 or the sensor device 30 (step S1302 to step S1312). This will be described in detail below.

The prediction unit 112 specifies a position of the user (step S1302). The position of the user indicates place where the user is relatively positioned with respect to the bed device 3 or a place where the user is positioned in the living room or the hospital room.

In the present embodiment, it is assumed that the position of the user indicates a relationship between the user and the bed device 3. For example, the following three cases are considered as the position of the user.

First Position: the user is inside the bed device 3. That is, the user is in a lying position, a half sitting position, and a long sitting position (posture).

Second Position: the user is outside the bed device 3. For example, the user is not limited to the standing state (posture). The user may use the wheelchair, the portable toilet, or the like. For convenience of description, in the following embodiment, a state in which the user is standing will be described as an example.

Third Position: the user is at an end of the bed device 3. That is, the user is in a sitting position (posture).

The position of the user may be determined, for example, by analyzing the image of the camera device 20, or may be determined according to a detection result of the sensor device 30. For example, it may be determined whether the user is at the second position or the first position using a bed-departure and on-bed sensor provided in the bed device 3. The position of the user may be detected by the load sensor provided in the bed device 3, and the first position or the third position may be determined.

Subsequently, the prediction unit 112 determines a feature amount to be used according to the position of the user (step S1304). Then, the prediction unit 112 acquires the feature amount determined in step S1304 from the acquisition unit (the surrounding environment acquisition unit 102, the posture acquisition unit 104, the motion acquisition unit 106, the biological information acquisition unit 108, and the disease information acquisition unit 110) or from the sensor device 30 (step S1306).

Subsequently, the prediction unit 112 determines whether there is a reduction factor (step S1308). Here, when it is determined that there is a reduction factor, the prediction unit 112 acquires the reduction factor (step S1308; Yes to step S1310). The prediction unit 112 may acquire the reduction factor from the acquisition unit, or may acquire the reduction factor from the image captured by the camera device 20.

The prediction unit 112 executes risk prediction processing (step S1312). When the risk prediction processing is executed, the prediction unit 112 predicts and outputs a risk for the user. In the present embodiment, the prediction unit 112 predicts (outputs) the risk of overturning and falling as the objective variable by using the prediction dictionary DB 1230, which is learned data, for example, with the acquired feature amount and the reduction factor as the explanatory variables. That is, in the present embodiment, the risk of overturning and falling is output as the risk for the user.

Figure 7:
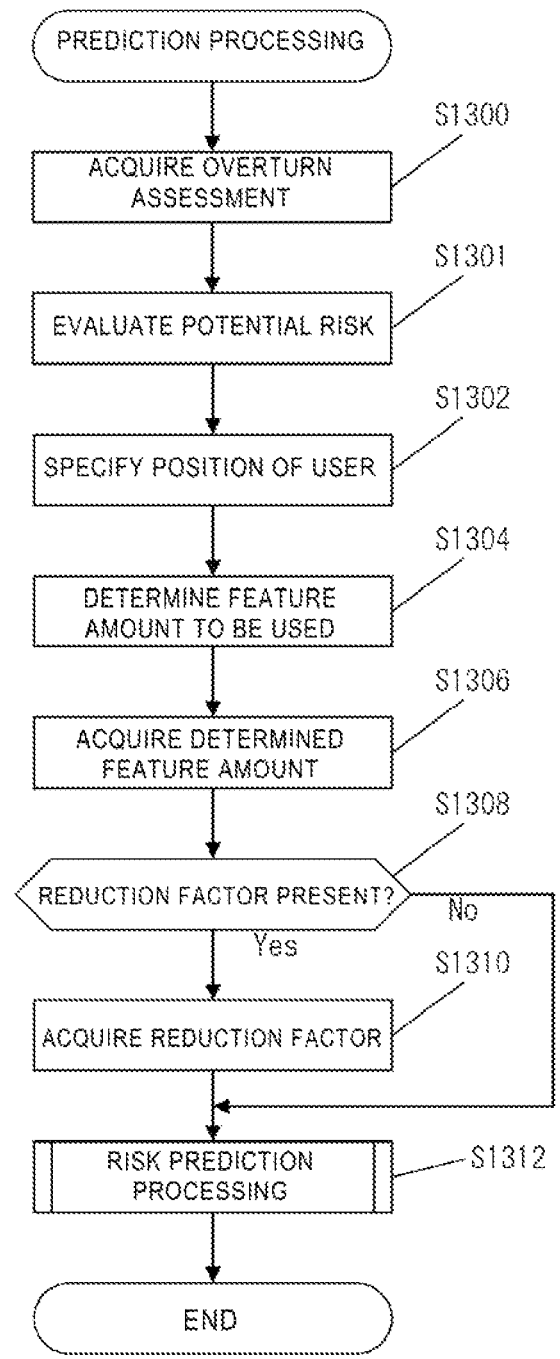
FIG. 7 is a diagram for illustrating prediction processing according to the first embodiment.

In FIG. 7 described above, the prediction unit 112 executes step S1302 after executing step S1300 and step S1301, whereas the present embodiment is not limited to this case. For example, step S1302 and the subsequent steps may be executed without executing step S1300 and step S1301. In this case, instead of the overturn assessment, the prediction unit 112 may acquire information equivalent to the assessment by using, for example, surrounding environment information acquired from the acquisition unit and the sensor device 30 (the surrounding environment information when the camera device 20 or the sensor device 30 is powered on, or a surrounding environment setting at a timing set by the staff or the like).

In FIG. 7, the prediction unit 112 determines the feature amount to be used according to the position of the user (step S1304) and acquires the determined feature amount (step S1306), whereas the present embodiment is not limited thereto. For example, the prediction unit 112 may acquire an image or the like from the acquisition unit or the sensor device 30 before the prediction processing starts. In this case, instead of step S1304 and step S1306 in FIG. 7, the prediction unit 112 may change a weighting for each feature amount according to the position of the user (weighted so that a weight of the feature amount to be used is increased), and then determine whether there is a reduction factor (step S1308). In other words, this example is different from FIG. 7 in that a feature amount other than the determined feature amount is also used.

A specific operation example in a case where the prediction unit 112 predicts the risk of overturning and falling by machine learning will be described later.

(7) Correspondence Execution Unit

The correspondence execution unit 114 executes an instruction according to the output of the prediction unit 112 to, for example, each device. For example, the correspondence execution unit 114 instructs each of the notifying unit 140, the terminal device 52, and the mobile terminal device 54 to appropriately perform notification as necessary, or instructs the display 130 to output advice.

Figure 8:
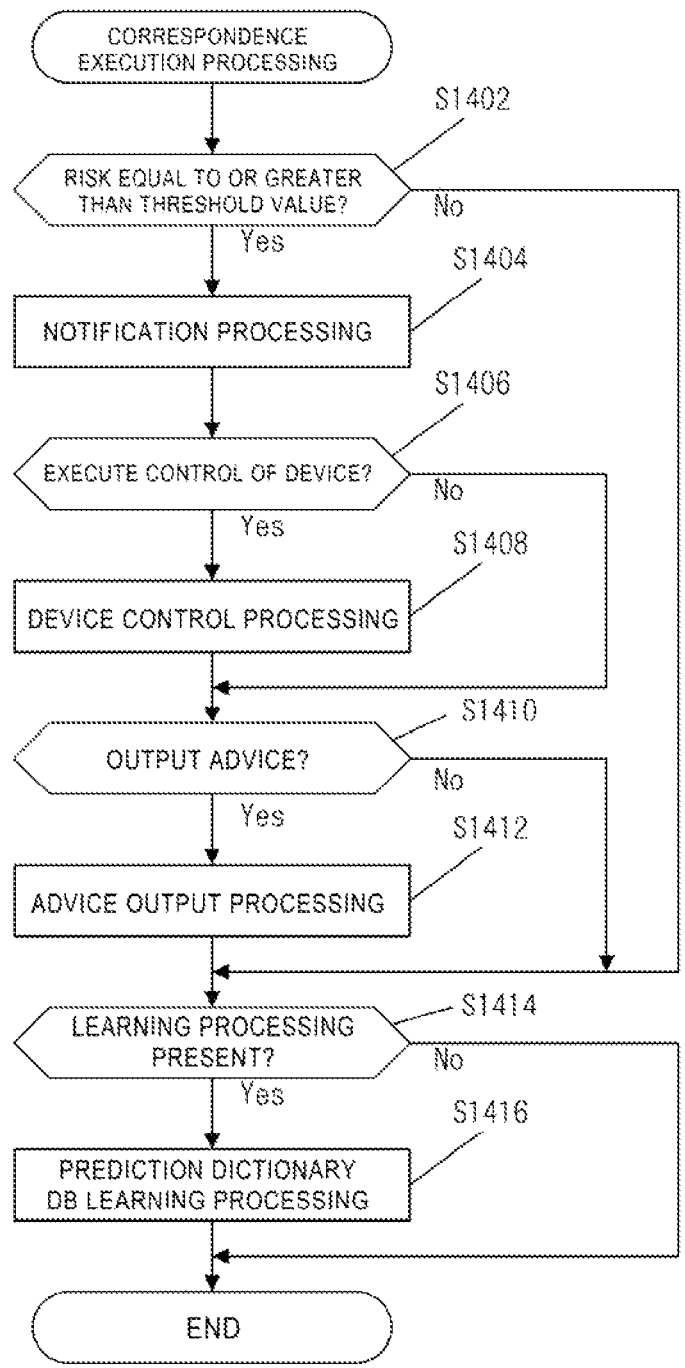
FIG. 8 is a diagram for illustrating correspondence execution processing according to the first embodiment.

An operation of correspondence execution processing executed by the correspondence execution unit 114 will be described with reference to FIG. 8. First, the correspondence execution unit 114 determines whether or not the risk is equal to or greater than a predetermined threshold value. In the present embodiment, the correspondence execution unit 114 determines whether or not the probability of the risk that causes the overturning and falling (hereinafter, simply referred to as "probability") is equal to or greater than the predetermined threshold value. Then, when the probability is equal to or greater than the threshold value, the correspondence execution unit 114 executes notification processing (step S1402; Yes to step S1404).

For example, when the probability is equal to or greater than the predetermined threshold value (preferably 40% to 60%), the correspondence execution unit 114 instructs the notifying unit 140 to notify that the risk of overturning and falling is high. The notifying unit 140 performs notification in response to the instruction.

The correspondence execution unit 114 may instruct other devices (the terminal device 52 and the mobile terminal device 54) to perform notification via the communicator 150. The correspondence execution unit 114 may instructs a device set by the staff or the like to perform the notification, or may change a device to which the instruction is issued according to the probability or the situation of the user or the staff.

For example, when the probability is equal to or greater than 40%, the correspondence execution unit 114 instructs only the notifying unit 140 to perform the notification. However, when the probability is equal to or greater than 50%, the correspondence execution unit 114 may instruct not only the notifying unit 140 but also the terminal device 52 and the mobile terminal device 54 to perform the notification. When each device performs the notification, the correspondence execution unit 114 may instruct only the mobile terminal device 54 of the staff who is available or is at a close distance to perform the notification.

As a notification method, the notifying unit 140 may output an alarm or notify by light emission or vibration. The notifying unit 140 may display a warning on the display 130. For example, the notifying unit 140 may announce attention on a layout or may notify the user of the warning by sound.

Subsequently, when it is necessary to give a control instruction to each device (step S1406), the correspondence execution unit 114 executes device control processing (step S1408). The correspondence execution unit 114 may instruct the bed control device 40 to automatically adjust the floor height of the bed or the angle of the back section by, for example, executing the device control processing. In addition to that, the correspondence execution unit 114 may instruct, for example, to automatically turn on foot lights up to a toilet or an exit, instruct to automatically switch a sensor setting button operation to an inoperable state, or instruct to automatically change the setting of the bed-departure sensor.

Subsequently, when the advice can be output, the correspondence execution unit 114 executes advice output processing using an overturning and falling DB (step S1410; Yes to step S1412). By executing the advice output processing, the correspondence execution unit 114 may automatically select, for example, equipment according to an overturn risk level, or may present a living room layout plan to, for example, a predetermined staff or a nearby staff.

Subsequently, when learning processing is executed, the correspondence execution unit 114 may execute the learning processing of the prediction dictionary DB 1230 (step S1414; Yes to step S1416). For example, the correspondence execution unit 114 instructs the display 130 to display that the risk of overturning and falling is high. At this time, when the staff or the like comes to cope with the situation but there is no possibility of overturning and falling of the user, the staff or the like inputs the fact that there is no possibility through the user interface device 135. On the other hand, when the notification is performed by the instruction of the correspondence execution unit 114, the staff or the like inputs that there is the actual risk of overturning and falling through the user interface device 135.

The information input by the staff and the like is stored in the prediction dictionary DB 1230. The correspondence execution unit 114 performs the machine learning and learns the prediction dictionary DB 1230 based on the information input by the staff or the like.

[1.2.2 Other Configurations]

The display 130 displays various kinds of information. For example, the display 130 is constituted by a liquid crystal display or an organic EL display. The display 130 may be another display device connected by HDMI (registered trademark) or D-SUB.

The user interface device 135 inputs various operations from the user, the staff, or the like. For example, an input device such as a manipulation remote controller or a nurse call is also included. A touch panel formed integrally with the display 130 also functions as the user interface device 135.

The notifying unit 140 performs the notification. For example, a speaker capable of outputting an alarm sound or a device that performs the notification by light or vibration may be used. The notifying unit 140 may perform the notification by sound output of a content to be notified, or by displaying a warning content on the display 130.

The communicator 150 communicates with other devices. For example, a LAN interface connected to a network, a USB connected to other devices, and a short-distance wireless communication unit are included. The communicator 150 may be a communication device connectable to a mobile phone communication network such as LTE/5G.

The camera device 20 is an image capturing device for capturing an image of a surrounding situation. The camera device 20 is capable of capturing a still image and a moving image.

The sensor device 30 can acquire the biological information of the user and the position and posture of the user by detecting the body motion or the like of the user. The sensor device 30 may acquire the biological information by detecting the load using the load sensor provided in the bed device 3.

The bed control device 40 controls the bed device 3. For example, the bed control device 40 implements a back raising motion/back lowering motion and a foot raising motion/foot lowering motion by controlling each section of the back section, the seat section, the upper leg section, and the lower leg section. The bed control device 40 can also change the floor height of the bed device 3.

The server device 50 stores the electronic medical record DB 502 in which the information on the disease of the user is stored. The server device 50 is a server that manages an in-hospital system, and may be, for example, a server of an electronic medical record server or an ordering system. In the electronic medical record DB 502 of the server device 50, in addition to basic information such as the name, date of birth, and blood type of the user, various pieces of information necessary for treatment such as disease history, examination history, surgical information, administration information, precautions, hospital visit history, and overturn history are stored. These pieces of information are merely examples, and the server device 50 does not necessarily need to store and manage the pieces of information. For example, the information related to surgery may be managed by a surgery management server (not shown). The information related to administration may be managed by an administration server (not shown).

The peripheral device 60 is provided in other device. For example, an IoT module can be mounted on an obstacle such as a wheelchair, a table, or a cane. These obstacles can be taken as the peripheral device 60 to output the positions of the obstacles and the like to the control device 10.

[1.3 Processing of Prediction Unit]

Here, the prediction processing executed by the prediction unit 112 according to the present embodiment will be described.

[1.3.1 Case Where User Is Inside Bed Device 3]

The case where the user is inside the bed device 3 (the case where the position of the user is the first position) will be described. That is, this is a case where the user is in a bed rest state (posture at lying position) or the like on the bed device 3. The posture of the user includes not only the posture at the lying position but also the posture at the long sitting position when the user gets up. The posture at the lying position may be any of a lateral position, a dorsal position, a prone position, a lateral position, and the like.

In this case, the prediction unit 112 determines the following points as feature amounts to be used, and acquires the determined feature amounts (steps S1304 and S1306 in FIG. 7).

(1) Motion

The prediction unit 112 acquires, from the motion acquisition unit 106, as the motion of the user, a feature amount regarding (i) whether or not the user is stretching his/her hand from the bed device 3 to the outside of the bed device 3, (ii) whether or not the user is riding over a fence or straddling the fence, (iii) whether or not the user is removing the fence, and (iv) whether or not the user is moving without operating the user interface device 135 (for example, whether or not the user gets up without operating the user interface device 135). Here, as the pattern of using the camera device 20 in the system 1, the pattern b, the pattern c, the pattern d, and the like among the patterns described with reference to FIGS. 2A to 2D may be used.

In the present embodiment, the case where the prediction unit 112 uses all of (i) to (iv) as the feature amount is described, whereas the present embodiment is not limited thereto, and a part of (i) to (iv) may be used. For example, the prediction unit 112 may use only number (i) and number (ii) or only number (i) and number (iii) as the feature amounts. The prediction unit 112 may give a lower priority to a higher number of number (i) to number (iv), and may weight the feature amounts in a descending order of priority. The prediction unit 112 may give a higher priority to a higher number of number (i) to number (iv), and may weight the feature amounts in an ascending order of priority.

(2) Reduction Factor

If there is a reduction factor, the prediction unit 112 acquires the reduction factor in the prediction processing (step S1308; Yes to step S1310). For example, the following may be considered as the reduction factor.

Regardless of whether or not the user stretches his/her hand from the bed device 3 to the outside of the bed device 3, if the bed device 3 used by the user is a low-floor bed, if the center of gravity or the head of the user is not outside the bed device 3, or if the user has a restraint band, it is determined that there is the reduction factor in the motion.

Regardless of whether or not the user is riding over the fence or straddling the fence, if the bed device 3 used by the user is a low-floor bed or if a mat for impact reduction is installed on a floor surrounding the bed device 3, it is determined that there is the reduction factor in the motion.

Regardless of whether or not the user removes the fence, if the fence is fixed to the bed device 3, it is determined that there is the reduction factor in the motion.

For example, the prediction unit 112 normally predicts that the risk is high when the user stretches his/her hand from the bed device 3 to the outside of the bed device 3. However, when the bed device 3 is the low-floor bed, the prediction unit 112 may predict that the risk related to the motion is low even when the user stretches his/her hand from the bed device 3 to the outside of the bed device 3.

When the bed device 3 is the low-floor bed, the prediction unit 112 may determine that there is the reduction factor, and predict a risk at a level lower than the risk level when the user stretches his/her hand from the bed device 3 to the outside of the bed device 3 for the risk related to the motion. As a result, the prediction unit 112 may predict the risk of overturning and falling as a level lower than that in the case where the user stretches his/her hand from the bed device 3 to the outside of the bed device 3.

That is, when there is the reduction factor, the prediction unit 112 predicts the risk at a level lower than a normally predicted level (low probability). For example, when the user stretches his/her hand from the bed device 3 to the outside of the bed device 3, the prediction unit 112 normally predicts that the risk of overturning and falling is "high". However, when there is the reduction factor such as the bed device 3 being the low-floor bed, the prediction unit 112 predicts that the risk of overturning and falling is lowered by one level to "medium". When the prediction unit 112 outputs the risk of overturning and falling with the probability, the prediction unit 112 may decrease the probability of the risk. For example, when there is no reduction factor, the prediction unit 112 outputs the probability of overturning and falling as "80%". However, when there is the reduction factor, the prediction unit 112 outputs the probability of overturning and falling as "60%".

In this manner, when there is another reduction factor, the prediction unit 112 outputs the risk at a level lower than the level of the risk of overturning and falling that is originally predicted (output), or outputs the risk at a value lower than the probability of overturning and falling that is originally output.

[1.3.2 Case Where User Is Outside Bed Device]

The case where the user is at a position outside the bed device 3, for example, the case where the user stands (the case where the position of the user is the second position) will be described. In this case, the prediction unit 112 determines the following points as feature amounts to be used, and acquires the determined feature amounts (steps S1304 and S1306 in FIG. 7).

(1) Surrounding Environment

The prediction unit 112 acquires, from the surrounding environment acquisition unit 102, (i) whether or not the user interface device 135 is at a position within the reach of the hand of the user as a feature amount. The surrounding environment acquisition unit 102 outputs the feature amount based on a distance between the position of the user interface device 135 and the position of the hand of the user or the like.

The prediction unit 112 acquires, from the surrounding environment acquisition unit 102, (ii) a degree of time until the staff or the like visits the user since the user operates the user interface device 135 as a feature amount. For example, the surrounding environment acquisition unit 102 calculates a time from when the camera device 20 detects that the user operates the user interface device 135 to when the camera device 20 recognizes the staff or the like, and outputs a feature amount based on the calculated time.

The prediction unit 112 acquires, from the surrounding environment acquisition unit 102, (iii) whether or not the position of the equipment is appropriate when there is the equipment (for example, a pedestrian or the portable toilet) as a feature amount. The surrounding environment acquisition unit 102 calculates and outputs the feature amount related to the position of the equipment based on, for example, the distance between the equipment and the bed device 3. Here, as the pattern of using the camera device 20 in the system 1, the pattern a, the pattern d, and the like among the patterns described in FIGS. 2A to 2D regarding the above (1) (iii) may be used. For the above (1) (i) and (ii), the pattern b, the pattern c, the pattern d, and the like, among the patterns described with reference to FIGS. 2A to 2D may be used.

In the present embodiment, the case where all of (i) to (iii) are used as the feature amounts is described, whereas the present embodiment is not limited thereto, and a part of (i) to (iii) may be used. For example, only the number (i) or only number (i) and number (ii) may be used as the feature amounts. A higher priority may be given to a lower number of number (i) to number (iii), and the feature amounts may be weighted in a descending order of priority. A higher priority may be given to a higher number of number (i) to number (iii), and the feature amounts may be weighted in the descending order of priority.

(2) Posture

The prediction unit 112 acquires, from the posture acquisition unit 104, (i) whether or not the center of gravity of the body of the user is biased as a feature amount. For example, a part of the user may have a paralyzed symptom. As a result, the center of gravity of the body of the user may be biased. The posture acquisition unit 104 calculates the center of gravity of the body based on the posture of the user, calculates the feature amount based on whether the center of gravity is biased to the left or right or to the front or back, and outputs the feature amount.

The prediction unit 112 acquires, from the posture acquisition unit 104, (ii) whether or not the user appropriately wears footwear as a feature amount. Here, as the pattern of using the camera device 20 in the system 1, the pattern b, the pattern c, the pattern d, and the like among the patterns described with reference to FIGS. 2A to 2D may be used.

In the present embodiment, the case where all of (i) and (ii) are used as the feature amounts is described, whereas the present embodiment is not limited thereto, and a part of (i) and (ii) may be used.

(3) Motion

The prediction unit 112 acquires, from the motion acquisition unit 106, as the motion of the user, a feature amount regarding (i) whether or not the user is standing without calling the staff or the like on the user interface device 135 (whether or not the user is standing without operating the user interface device 135), (ii) whether or not the user is standing in an unbalanced state, (iii) whether or not the motion from the standing state until the user takes the posture of a sitting position in the bed device 3 is appropriately performed when the user enters the bed device 3, (iv) whether or not the user is shaking, (v) whether or not the user is trying to remove or removes a supportive device, and (vi) whether or not the user is incontinence. Here, as the pattern of using the camera device 20 in the system 1, the pattern b, the pattern c, the pattern d, and the like among the patterns described with reference to FIGS. 2A to 2D may be used.

In the present embodiment, the case where all of (i) to (vi) are used as the feature amounts is described, whereas the present embodiment is not limited thereto, and a part of (i) to (vi) may be used. For example, only number (i) or only number (i) and number (ii) may be used as the feature amounts. A higher priority may be given to a lower number of number (i) to number (iii), and the feature amounts may be weighted in a descending order of priority. A higher priority may be given to a larger number of number (i) to number (iii), and the feature amounts may be weighted in the descending order of priority.

(4) Reduction Factor

If there is a reduction factor, the prediction unit 112 acquires the reduction factor in the prediction processing (step S1308; Yes to step S1310). For example, the following may be considered as the reduction factor.

Regardless of whether or not the center of gravity of the body of the user is biased, the prediction unit 112 determines that, if the user grasps a stable item (for example, a fixed equipment), there is a reduction factor as to whether or not the center of gravity of the body of the user is biased. Even if the user does not grasp the stable item, if the bias of the center of gravity of the body of the user is reduced, the prediction unit 112 determines that there is the reduction factor.

Regardless of whether the motion from the standing state until the user takes the posture of the sitting position in the bed device 3 is appropriately performed when the user enters the bed device 3, the prediction unit 112 determines that, if the mat for impact reduction is installed on the floor surrounding the bed device 3, there is a reduction factor as to whether or not the motion is performed appropriately.

For these reduction factors, the motion acquisition unit 106 may determine a motion serving as the reduction factor, or may output a feature amount indicating the reduction factor. In this manner, the prediction unit 112 outputs the risk at a level lower than the level of the originally output risk of overturning and falling, or outputs the risk at a probability lower than the originally output probability of overturning and falling.

[1.3.3 Case Where User Is in Sitting Position in Bed Device 3]

The case where the user is in the sitting position in the bed device 3 (the case where the position of the user is the third position) will be described.

In this case, the prediction unit 112 determines the following points as feature amounts to be used, and acquires the determined feature amounts (steps S1304 and S1306 in FIG. 7).

(1) Surrounding Environment

The prediction unit 112 acquires, from the surrounding environment acquisition unit 102, (i) whether or not the setting information of the sensor used for the user is set to a level lower than the setting information of the sensor of the overturn assessment as a feature amount. Examples of the sensor include a mat sensor placed on a bed or the floor and a sheet sensor (body motion sensor) placed under the mattress 4, and include various sensors.

The setting information of the sensor used for the user being set to the level lower than the setting information of the sensor of the overturn assessment means that the actually installed sensor is not appropriate compared to the setting information of the sensor necessary for the overturn assessment.

For example, a case where an appropriate sensor is not provided to the user (an appropriate sensor is not installed or the type is different), and therefore, only the information that can be acquired from the sensor used by the user is insufficient from a viewpoint of the information that can be acquired from the sensor of the overturn assessment. Alternatively, a case where no sensor is installed when it is desired to detect the getting up of the user.

Even if the appropriate sensor is provided to the user, a case where an appropriate setting is not made for the user among a plurality of settings of the sensor may be included. For example, when the mat sensor for detecting bed-departure is installed surrounding the bed device 3, or when the sheet sensor is appropriately provided to the user, it is necessary to set a notification when the sheet sensor detects the getting up, but it is set to detect when the user departs from the bed. The surrounding environment acquisition unit 102 outputs, as a feature amount, that the level is set to be low based on the setting information of the sensor of the overturn assessment and the setting information of the sensor used by the user.

The prediction unit 112 acquires, from the surrounding environment acquisition unit 102, (ii) whether or not the motion to be detected by the sensor is correctly detected as a feature amount. The surrounding environment acquisition unit 102 calculates and outputs a feature amount based on whether or not respective results match based on a detection result of the sensor and a result of the image captured by the camera device 20. For example, when the bed-departure of the user is to be detected by the sensor, but the sensor does not detect even when the user departs from the bed, and it can be determined from the image of the camera device 20 that the user departs from the bed, the surrounding environment acquisition unit 102 determines that the motion to be detected by the sensor is not correctly detected, and outputs, for example, a flag "1" as the feature amount.

The prediction unit 112 acquires, from the surrounding environment acquisition unit 102, (iii) whether or not the type of fence used by the user is an appropriate type (a type of fence set in the overturn assessment), and whether or not the number of fences used by the user is equal to or greater than the number of fences set in the overturn assessment, as feature amounts. The surrounding environment acquisition unit 102 calculates and outputs the feature amounts based on whether the number of fences used by the user is equal to or greater than the number of fences set in the overturn assessment, whether the type of fence used by the user is an appropriate type, and the like based on the set number and the type of the overturn assessment and the image captured by the camera device 20.

The prediction unit 112 acquires, from the surrounding environment acquisition unit 102, (iv) whether or not the user appropriately wears the supportive device as a feature amount.

The prediction unit 112 acquires, from the surrounding environment acquisition unit 102, as feature amounts, (v) when there is the equipment (for example, the wheelchair or the table), whether or not the equipment is locked, (vi) whether or not the obstacle (for example, a carrying object of the user himself/herself) is dropped on the floor surrounding the bed device 3, (vii) whether or not the user is appropriately wearing clothing (for example, whether or not a button of the clothing is displaced or has come undone), and (viii) whether or not the user interface device 135 is arranged at a predetermined position. The surrounding environment acquisition unit 102 may determine whether or not the user interface device 135 is arranged at the predetermined position based on the distance between the position of the user interface device 135 and the position of the hand of the user.

In the present embodiment, the case where all of (i) to (viii) are used as the feature amounts is described, whereas the present embodiment is not limited thereto, and a part of (i) to (viii) may be used. For example, only number (i) to number (v) or only number (i), number (iii), and number (v) may be used as the feature amounts. A higher priority may be given to a lower number of number (i) to number (viii), and the feature amounts may be weighted in a descending order of priority. A higher priority may be given to a higher number of number (i) to number (viii), and the feature amounts may be weighted in the descending order of priority.

Here, various patterns of using the camera device 20 in the system 1 are conceivable. For example, in order to acquire the above (1) (v) and (vi), the pattern a, the pattern d, and the like among the patterns described with reference to FIGS. 2A to 2D may be used in the system 1. In order to acquire the above (1) (i), (ii), (iii), (iv), (vii), and (viii), the pattern b, the pattern c, the pattern d, and the like among the patterns described with reference to FIGS. 2A to 2D can be used in the system 1.

(2) Posture

The prediction unit 112 acquires, from the posture acquisition unit 104, a feature amount regarding (i) whether or not the user is sitting deeply (positions of a waist and a hip). Here, as the pattern of using the camera device 20 in the system 1, the pattern b, the pattern c, the pattern d, and the like among the patterns described with reference to FIGS. 2A to 2D may be used.

(3) Motion

The prediction unit 112 acquires, from the motion acquisition unit 106, as the motion of the user, a feature amount regarding (i) whether or not the user is performing a motion of departing from the bed appropriately (for example, whether or not the user is performing a motion of sliding down from the bed with a lower body outside the bed device 3 while an upper body of the user is not raised), (ii) whether or not the user is trying to depart from the bed without calling the staff or the like by the user interface device 135 (whether or not the user is trying to depart from the bed without operating the user interface device 135), (iii) whether or not the user is shaking, (iv) whether or not the user is trying to depart from the bed without wearing the footwear, (v) whether or not the user is trying to put his/her hand on the equipment in the case where there is the equipment, and (vi) whether or not the user is trying to pick up an object surrounding the bed device 3 (for example, an object which is carried by the user himself/herself, an object on the floor or in a low place, which is a broader concept than the obstacles illustrated above).

Here, as the pattern of using the camera device 20 in the system 1, the pattern a, the pattern d, and the like among the patterns described in FIGS. 2A to 2D may be used for (3) (iv), and (vi) described above. As the pattern of using the camera device 20 in the system 1, the pattern b, the pattern c, the pattern d, and the like among the patterns described in 2A to 2D may be used for (3) (i), (ii), (iii), (iv), and (v) described above.

In the present embodiment, the case where all of (i) to (vi) are used as the feature amounts is described, whereas the present embodiment is not limited thereto, and a part of (i) to (vi) may be used. For example, only number (i) and number (ii) or only number (i), number (iii), and number (v) may be used as feature amounts. A higher priority may be given to a lower number of number (i) to number (vi), and the feature amounts may be weighted in a descending order of priority. A higher priority may be given to a higher number of number (i) to number (iv), and the feature amounts may be weighted in the descending order of priority.

(4) Reduction Factor

If there is a reduction factor, the prediction unit 112 acquires the reduction factor in the prediction processing (step S1308; Yes to step S1310). For example, the following may be considered as the reduction factor.

Regardless of whether or not an object (for example, the carrying object of the user himself/herself) drops on the floor surrounding the bed device 3, if the user is trying to depart from the bed without looking at the obstacle, the prediction unit 112 determines that there is a reduction factor as to whether or not the obstacle (for example, a carrying object of the user himself/herself) drops on the floor surrounding the bed device 3.

In a case where there is the equipment, regardless of whether or not the user is trying to put his/her hand on the equipment, if the equipment is locked, the prediction unit 112 determines that there is a reduction factor as to whether or not the user is trying to put his/her hand on the equipment.

In this manner, when it is determined that there is the reduction factor, the prediction unit 112 can output the risk at a level lower than the level of the originally output risk of overturning and falling, or at a probability lower than the originally output probability of overturning and falling.

[1.3.4 Risk Prediction Processing]

Then, the prediction unit 112 executes the risk prediction processing using the feature amount acquired in step S1306 and the reduction factor acquired in step S1310 as the explanatory variables (step S1312). By executing the risk prediction processing, the prediction unit 112 outputs the overturning and falling risk as the objective variable using the prediction dictionary DB 1320 based on the explanatory variables.

[1.3.5 Other Reduction Factors]

Other reduction factors may be output. For example, in a case where the staff or the like is present near the user or in a case where it is possible to determine that the overturning and falling risk is low according to the situation of the disease, the prediction unit 112 determines that there is the reduction factor.

[1.4 Device Control Processing]

Some examples of the device control processing (step S1408 in FIG. 8), which is one of the processing executed by the correspondence execution unit 114, will be described.

The controller 100 (the correspondence execution unit 114) can execute processing of controlling other devices or the like by executing the device control processing. In the device control processing, the controller 100 may execute the following processing based on a value output from the prediction unit 112. In the device control processing, the controller 100 may execute the following processing by analyzing the image captured by the camera device 20.

(1) The controller 100 may stop the currently operating processing or switch the processing to different processing. For example, when the controller 100 executes rotation processing and a rotation operation is being performed, when the probability of overturning and falling is equal to or greater than the threshold value (step S1402; Yes), the rotation operation may be stopped. When the probability of overturning and falling is equal to or greater than the threshold value (step S1402; Yes), the controller 100 may change the control to delay the rotation operation being executed or to switch an expansion and contraction pattern of a cell.

For example, the controller 100 may execute the rotation operation by expanding and contracting a sub-air cell for rotation placed on or below the mattress 4. The controller 100 may implement the rotation operation by changing the angle of the section of the bed device 3, or may implement the rotation operation by inclining the section.

(2) Furthermore, the controller 100 may not only simply stop the rotation operation, but also change the control according to the acquired posture of the user or the like. For example, when it is determined that the posture of the user does not change for a predetermined time, the controller 100 may perform the rotation operation. At this time, although the controller 100 controls the sub-air cell so as to have a preset angle, when it is determined from the image received from the camera device 20 that the posture of the user does not change, an air cell may be expanded or contracted so that the angle of change becomes larger. When the controller 100 determines that the posture of the user greatly changes from the image received from the camera device 20, the controller 100 may expand or contract the air cell so that the angle of change due to the rotation operation becomes small, or may stop the air cell.

(3) The controller 100 acquires the prohibited behavior of the user based on the disease information acquired from the disease information acquisition unit 110. Then, as the motion of the user, when the prohibited behavior of the user is detected from the image received from the camera device 20, the controller 100 performs an operation of notifying the user via the notifying unit 140.

(4) The controller 100 analyzes the behavior of the user from the image captured by the camera device 20. Then, the controller 100 changes a shape of the bed device 3 (section) by controlling the bed control device 40 according to the behavior of the user. For example, when the controller 100 recognizes that a meal is served to the user from the image received from the camera device 20, the controller 100 raises the back section to set the back section to a predetermined back raising angle so as to have a shape appropriate for the user to have the meal. The controller 100 matches the shape of the bed device 3 with the time point and controls the shape of the bed device 3 for each predetermined time point. At this time, the controller 100 may or may not change the shape of the bed device 3 according to the state of the user recognized via the camera device 20 even when the predetermined time point comes.

2. Second Embodiment

A second embodiment will be described. The first embodiment is an embodiment in which various kinds of processing are executed in the control device 10. The second embodiment is an embodiment in which various kinds of processing are executed by a server device. In the present embodiment, only portions different from those of the first embodiment will be described, and components having common functions are denoted by the same reference numerals, and description thereof will be omitted.

Figure 9:
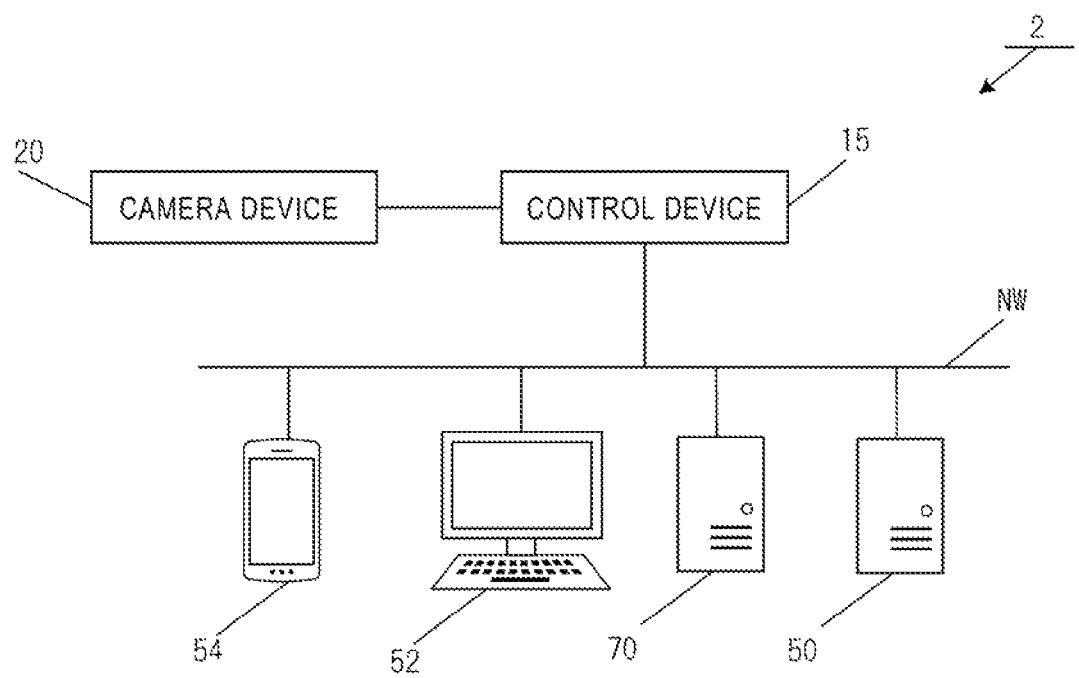
FIG. 9 is a diagram showing an overall system according to a second embodiment.

FIG. 9 is a partial diagram illustrating an overview of a system 2 according to the second embodiment. In the second embodiment, a control device 15 is connected to the network NW. In addition to the camera device 20, various devices are connected to the control device 15. A server device 70 executes overturning and falling prediction processing and the like. The server device 70 is connected to the network NW.

Figure 10:
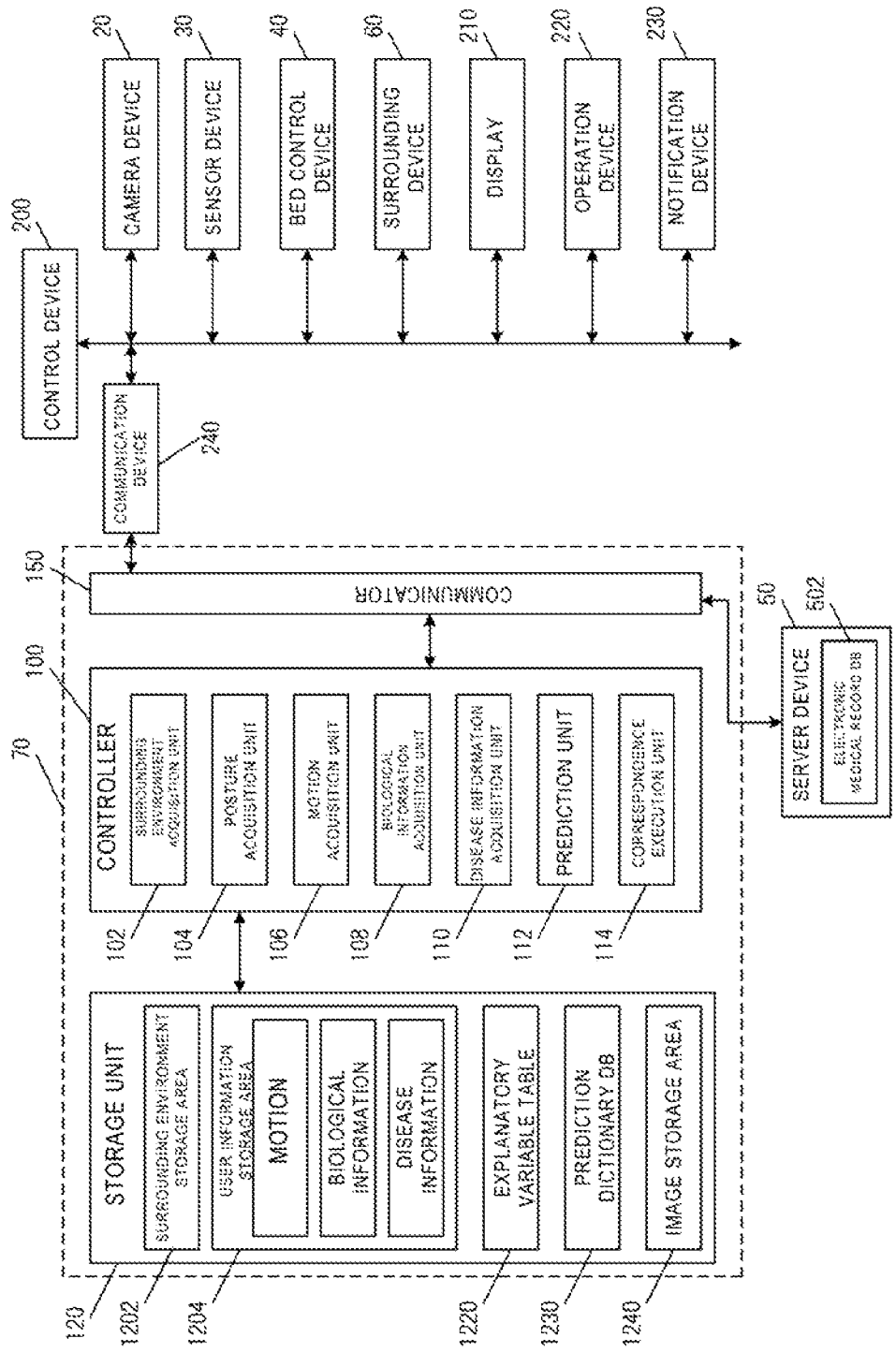
FIG. 10 is a diagram for illustrating a functional configuration according to the second embodiment.

FIG. 10 is a diagram for illustrating functions according to the second embodiment. The processing performed by the control device 10 in the first embodiment is implemented by the server device 70.

That is, a living room includes a control device 200 including a controller, and each device is connected to the control device 200. A display 210 corresponds to the display 130 in the first embodiment. An operation device 220 corresponds to the user interface device 135 in the first embodiment. A notification device 230 corresponds to the notifying unit 140 in the first embodiment. A communication device 240 corresponds to the communicator 150 in the first embodiment. Each device may be formed integrally with the control device 200 or may be constituted as a separate device.

In the second embodiment, data acquired by various devices is transmitted to the server device 70. For example, an image captured by the camera device 20 is transmitted from the control device 200 to the server device 70. The server device 70 stores the received image in the image storage area 1240. Similarly, for example, a signal indicating a body motion acquired by the sensor device 30 is also transmitted to the server device 70.

Then, in the server device 70, the prediction unit 112 predicts a probability of the risk of overturning and falling based on received various signals and information. Then, the correspondence execution unit 114 executes notification processing or the like on the notification device 230.

As described above, according to the present embodiment, the functions described in the first embodiment can also be implemented by the server device 70 or a cloud. In the present embodiment, all the functions implemented in the first embodiment are implemented by the server device 70, whereas only a part of the functions implemented by the control device 10 in the first embodiment may be implemented by the server device 70. For example, the biological information acquisition unit 108 and the disease information acquisition unit 110 may be implemented by the control device 200, and other functions may be implemented by the server device 70.

3. Third Embodiment

A third embodiment is an embodiment in which acquisition of a feature amount by the camera device 20 and acquisition of a feature amount by the sensor device 30 are combined. Description of configurations common to the first embodiment and the second embodiment will be omitted, and different configurations will be described below.

In the third embodiment, the sensor device 30 is provided for each of the bed device 3, peripheral devices, and equipment as necessary. Then, the controller 100 (the prediction unit 112) can select the acquisition of the feature amount from the camera device 20 and the acquisition of the feature amount from the sensor device 30 as necessary.

For example, the surrounding environment acquisition unit 102 may acquire a mounting state of the side rail 6, an assistance bar, and the like based on information from the sensor device 30 instead of the camera device 20. Specifically, the sensor device 30 is a pressure sensor that detects a pressure applied to a portion having an option receiver. In this case, the surrounding environment acquisition unit 102 determines whether or not the side rail 6 is mounted based on the pressure detected by the pressure sensor.

The sensor device 30 may be a contact sensor provided in a lower portion of the option receiver. In this case, the surrounding environment acquisition unit 102 determines whether or not the side rail 6 is mounted by the contact sensor detecting that the side rail 6 is in contact.

The sensor device 30 may be a direction detection sensor provided in the assistance bar. In this case, the direction detection sensor detects a direction of the assistance bar, so that the surrounding environment acquisition unit 102 determines whether or not the direction of the assistance bar is correct.

The sensor device 30 may be a sensor that detects connection with the board 5. For example, in a configuration of JP-A-2017-42398 (Filing date: Aug. 27, 2015, Title of invention: Brake device in bed device), a wire that can be energized is used as a brake wire. The sensor device 30 detects whether the board 5 is installed on the bed device 3 or locked based on an energization state of the brake wire.

In the system 1, the contact sensor may be provided at each place as the sensor device 30. For example, the position of the hand of the user may be detected by providing the contact sensor on the side rail 6 or the assistance bar. The pressure sensor may be arranged surrounding the bed device 3 to detect that the foot of the user touches the floor.

In the system 1, a position detection sensor may be provided in the peripheral device (peripheral device 60) or the equipment as the sensor device 30. The sensor device 30 may detect the position of the peripheral device (peripheral device 60) or the equipment in the living room or a hospital room as a relative position with respect to the bed device 3.

The controller 100 may acquire a floor height of the bed device 3 from the bed control device 40.

As described above, when the controller 100 acquires the feature amount, the controller 100 may acquire the feature amount based on the image captured by the camera device 20, or may acquire the feature amount from the sensor device 30, the bed control device 40, or the peripheral device 60.

Accordingly, it is possible to perform detection with higher accuracy or more reliably in a case where detection is performed by another device than in a case where detection is performed based on the image captured by the camera device 20. By combining the camera device 20 and the sensor device 30 or the like, it is possible to reduce processing (processing such as image analysis) in the controller 100, and it is possible to speed up the overall processing.

4. Fourth Embodiment

In a fourth embodiment, an embodiment in which boards 5 having a plurality of positions of the camera device 20 are used in combination will be described. Description of configurations common to those of the above-described embodiments will be omitted, and different configurations will be described below.

FIGS. 11A to 11D are diagrams for illustrating positions of the camera device 20 arranged on the board 5. In the board 5 (first board) illustrated in FIG. 11A, one camera device 20a (camera device 20) is fixedly arranged in a center or in the vicinity of the center.

Figure 11A:
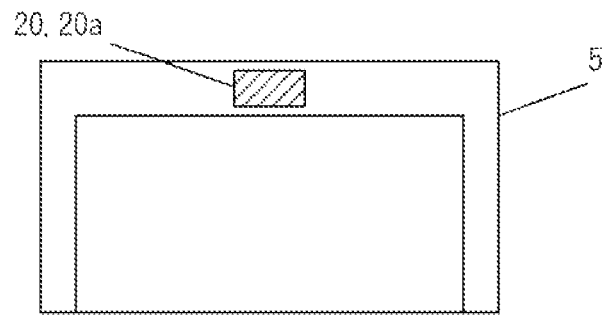
FIGS. 11A to 11D are diagrams for illustrating arrangement (positions) of camera devices according to a fourth embodiment.
Figure 11B:
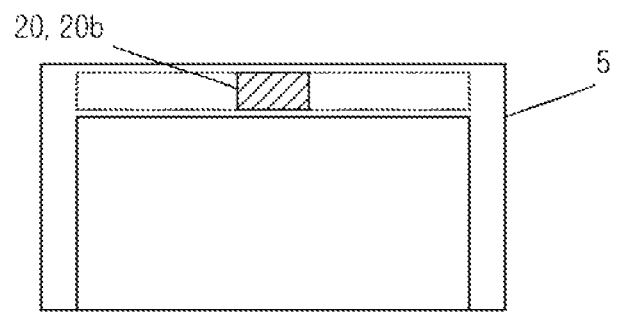

In the board 5 (second board) illustrated in FIG. 11B, one camera device 20b (camera device 20) is arranged so that it can be moved from a right end to a left end.

Figure 11C:
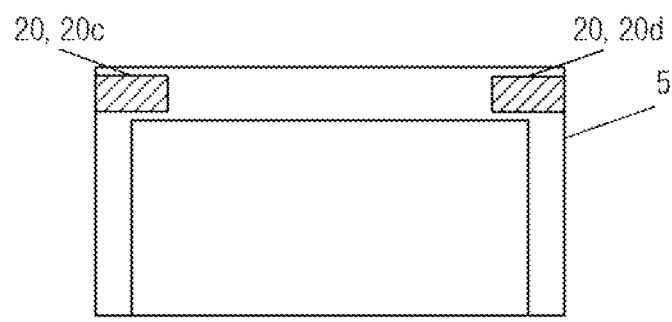

In the board 5 (third board) illustrated in FIG. 11C, two camera devices 20c and 20d are arranged at the left and right ends or in the vicinity of the ends.

Figure 11D:
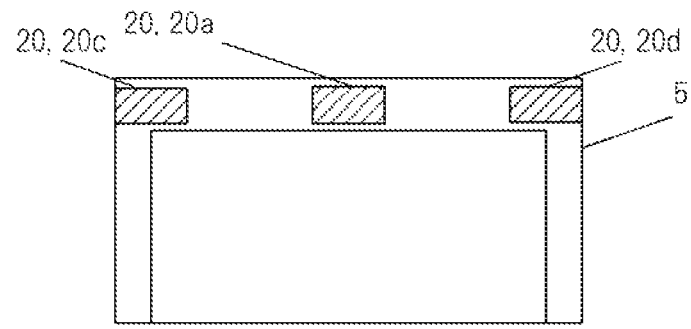

The board 5 (fourth board) illustrated in FIG. 11D is provided with three camera devices 20. For example, as illustrated in the first board, the camera device 20a is arranged at the center or in the vicinity of the center, and the camera device 20c and the camera device 20d are arranged at the left and right ends or in the vicinity of the ends.

By combining the boards 5, the system 1 can appropriately recognize the user on the bed device 3.

For example, when the first board is used as the head board, the user on the bed device 3 can be recognized by using the third board as the foot board. By using the second board or the fourth board as the head board, the camera device 20 may not be mounted on the foot board, or the foot board itself may not be mounted on the bed device 3.

5. Fifth Embodiment

A fifth embodiment is an embodiment in which, when a plurality of bed devices 3 are installed, a camera installed in a place other than the bed device 3 used by the user is used.

Figure 12:
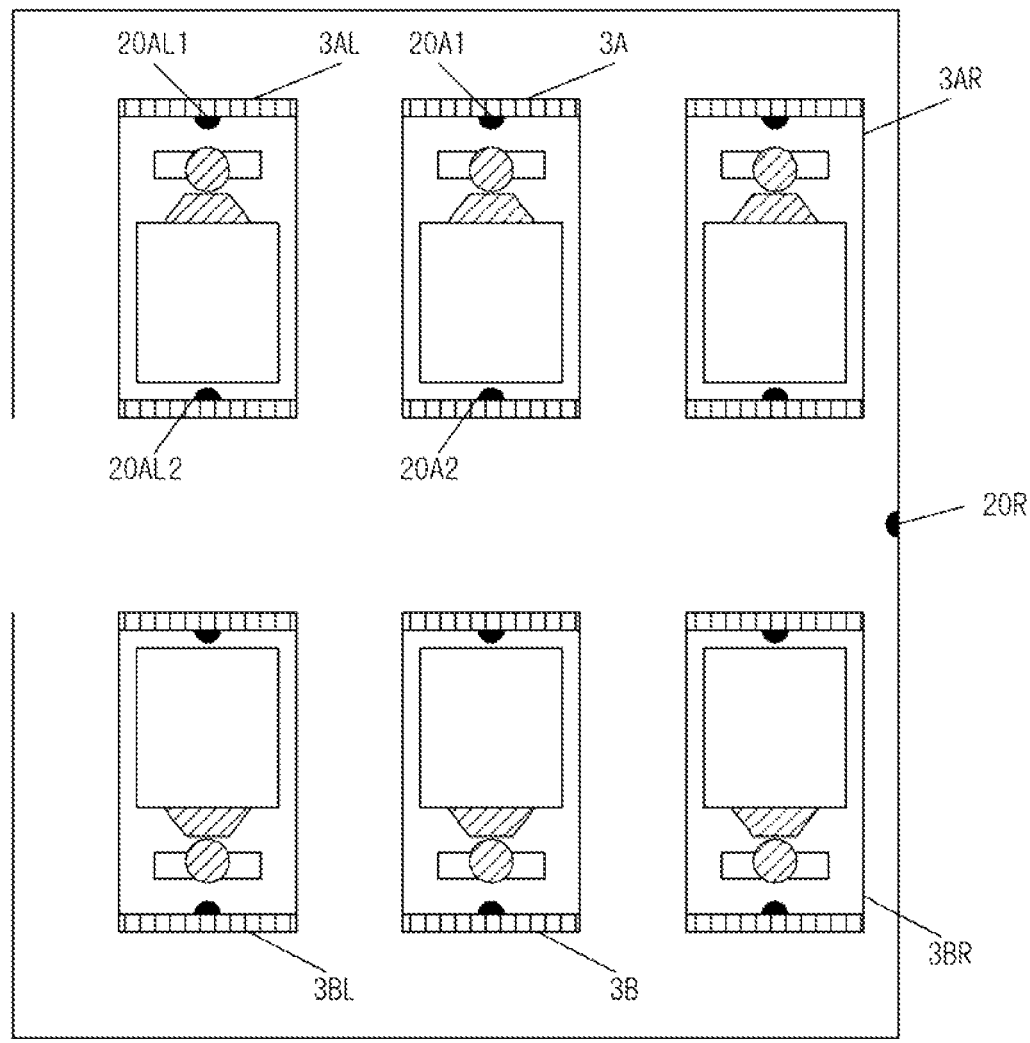
FIG. 12 is a diagram for illustrating an operation example according to a fifth embodiment.

FIG. 12 is a schematic diagram illustrating an entire living room or hospital room. FIG. 12 shows an example of the hospital room in which six bed devices 3 are provided. For example, in the case of a bed device 3A used by a target user, the bed device 3A is provided with a camera device 20A1 and a camera device 20A2.

The bed devices are also arranged around the bed device 3A. A bed device 3B is arranged on a side facing the bed device 3A (lower side in FIG. 12). A bed device 3AR is arranged on the right side of the bed device 3A in the drawing. A bed device 3AL is arranged on the left side of the bed device 3A in the drawing.

A bed device 3BR is arranged on the right side of the bed device 3B, which is arranged to face the bed device 3A, in the drawing. A bed device 3BL is arranged on the left side of the bed device 3B in the drawing.

Each bed device 3 is provided with cameras as necessary. For example, in the bed device 3AL, a camera device 20AL1 is provided on the head board, and a camera device 20AL2 is provided on the foot board. A camera device 20R capable of capturing an image of the entire hospital room may be provided on a wall in the room.

Figures 13A, 13B:
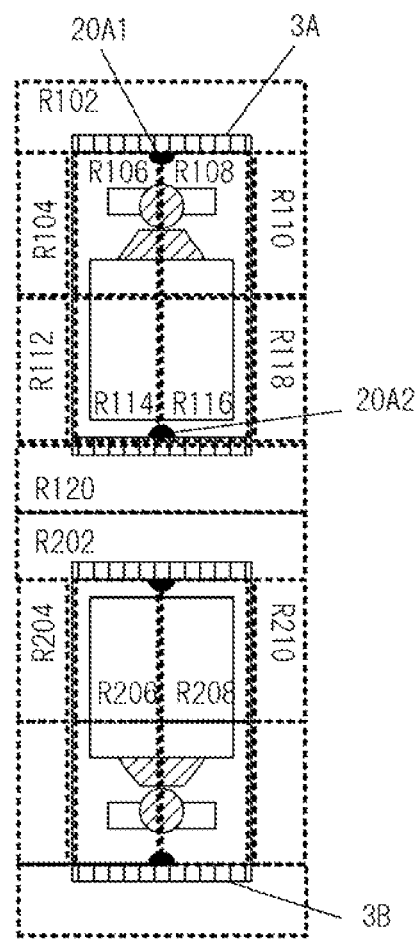
FIGS. 13A and 13B are diagrams for illustrating the operation example according to the fifth embodiment.

The storage unit 120 stores a range (capture range) that can be captured by each camera device 20 in a table (capturing range table). FIG. 13A shows an example of a capturing range table 1250.

The capturing range table 1250 stores identification information for specifying the camera, a position where the camera is installed, and the capture range.

Here, the capture range may store, for example, coordinates in a case where the hospital room is expressed in an XY space, or may be indicated by an area set in advance. The controller 100 may calculate by analyzing an image captured by the camera device 20, and may store the capture range based on a calculated result.

For example, as illustrated in FIG. 13B, an area including the surrounding of the bed device 3A is virtually set. In FIG. 13B, the following areas are set.

Area R102: an area on the head side outside the bed device 3A

Area R104: an area on the left side of the drawing on the head side (upper body) outside the bed device 3A Area R106: an area on the left side of the drawing on the head side (upper body) in the bed device 3A Area R108: an area on the right side of the drawing on the head side (upper body) in the bed device 3A Area R110: an area on the right side of the drawing on the head side (upper body) outside the bed device 3A Area R112: an area on the left side of the drawing on the foot side (lower body) outside the bed device 3A Area R114: an area on the left side of the drawing on the foot side (lower body) in the bed device 3A Area R116: an area on the right side of the drawing on the foot side (lower body) in the bed device 3A Area R118: an area on the right side of the drawing on the foot side (lower body) outside the bed device 3A Area R120: an area on the foot side outside the bed device 3A An area may be virtually set for all of the bed device 3B and other bed devices. In FIG. 13B, only areas R202, R204, R206, R208, and R210 necessary for description are denoted by reference numerals.

Here, the controller 100 can acquire a range in which capturing by the camera device 20A1 provided in the bed device 3A is possible by referring to the capturing range table 1250. According to the capturing range table 1250 in FIG. 13A, the range that can be captured by the camera device 20A1 is the range of the areas R112 to R120 and the areas R202 to R210.

Accordingly, the controller 100 can specify a range in which a surrounding situation is acquired or the posture and the motion of the user are acquired by using the camera device 20A1. When the range to be captured by only the camera device 20 of the bed device 3 used by the user is insufficient, the controller 100 acquires an image in cooperation with the camera device 20 provided in another device.

Figure 14:
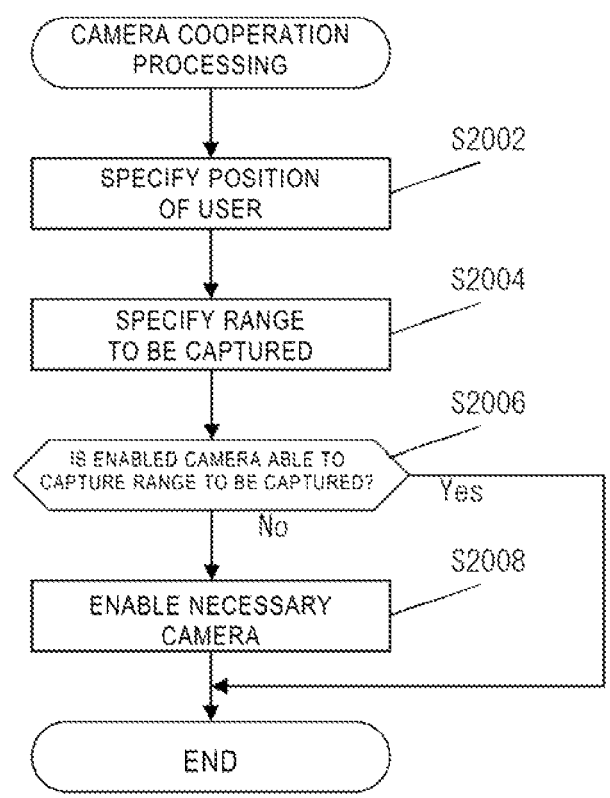
FIG. 14 is a flowchart for illustrating processing according to the fifth embodiment.

FIG. 14 is an example of an operation flow of camera cooperation processing executed by the controller 100. For example, the controller 100 specifies the position of the user (step S2002). At this time, a range to be captured is specified as a range necessary for determining a risk necessary for acquiring the posture and the motion of the user (step S2004). The controller 100 may specify a capturing range necessary for acquiring the surrounding environment of the user. The controller 100 determines whether or not the capturing range specified in step S2004 can be captured by a currently enabled camera device 20 (step S2006). Here, the enabled camera refers to the following camera.

- Camera device 20 provided in bed device 3 used by the user
- Camera device 20 whose power supply is turned on
- Camera device 20 that is not provided in the bed device 3 but is already capable of acquiring an image by the controller 100

When the camera device 20 necessary for capturing the capturing range specified in step S2004 is not enabled, the controller 100 refers to the capturing range table 1250 and enables a necessary camera (step S2006; Yes to step S2008).

Enabling the necessary camera includes turning on the power supply of the camera device 20 by the controller 100. Enabling the necessary camera also includes enabling the controller 100 to acquire an image from the camera device 20 provided in another device, for example, the camera device 20AL1 provided in the bed device 3AL or the camera device 20R provided in the hospital room.

As described above, according to the present embodiment, it is possible to install not only the camera device 20 provided in the bed device 3 but also the camera device 20 in consideration of the arrangement of the living room, the hospital room, and the entire facility. The controller 100 can acquire the posture and the motion of the user, and the surrounding environment from not only the camera installed in the bed device 3, but also the camera installed in another device in cooperation.

It is possible to switch the state of the camera device 20 as necessary. For example, the control device 10 normally turns off the power supply of the camera device 20. Then, when the position of the user is included in the vicinity of the bed device 3, the power supply of the camera device 20 may be turned on and the state of the camera device 20 may be switched as enabled.

In this case, for example, when the bed device 3 includes a plurality of camera devices 20, only the camera device 20 capable of capturing an image of a position to which the user approaches may be enabled, and other camera devices 20 may be disabled (power supply turned off) in order to reduce power consumption. The position of the user may be specified by using the camera device 20 provided in the living room or the hospital room.

The control device 10 may enable all the camera devices 20 necessary for acquiring the posture and the motion of the user. For example, the camera devices 20 provided in the bed devices 3 installed adjacent to the bed device 3 used by the user and the bed device 3 installed facing the bed device 3 used by the user may be enabled.

An operation example will be described with reference to FIG. 15. FIG. 15 is a diagram illustrating a relationship between the bed device 3A and the bed device 3B installed to face the bed device 3A. For example, in the bed device 3A, one camera device 20A1 is provided in the vicinity of the center of a head board 5A1. Here, the capturing range of the camera device 20A1 is set at a position where the bed device 3B arranged facing the bed device 3A is included. Similarly, one camera device 20B is provided in the vicinity of the center of a head board 5B1 of the bed device 3B. The camera device 20B is installed at a position where the bed device 3A is included in the capturing range.

Then, the system 1 causes the camera device 20A and the camera device 20B to cooperate with each other, so that the user on the bed device 3A can be recognized without arranging the camera device 20 on a foot board 5A2 of the bed device 3A. The user on the bed device 3B can be recognized without arranging the camera device 20 on a foot board 5B2 of the bed device 3B.

In FIG. 15, the bed devices 3 facing each other are described as an example, whereas the camera devices 20 provided in the adjacent bed devices 3 may be cooperated with each other. For example, in FIG. 12, the control device 10 of the first bed device 3A determines that the user has a bed-departure behavior in step S2002 in FIG. 14.

The bed-departure behavior of the user may be determined by the posture acquisition unit 104 acquiring that the user has reached the posture of the sitting position. The motion acquisition unit 106 may determine that the user has the bed-departure behavior using a sensor.

Here, the control device 10 further specifies a direction in which the user departs from the bed. For example, in FIG. 12, when it is determined that the user departs from the bed device 3A on the left side of the drawing, an area where the bed device 3AL is present is also included in the capturing range.

In this case, the control device 10 cooperates with the camera of the bed device 3AL. That is, in step S2006 in FIG. 14, the controller 100 of the control device 10 determines that the capturing range can be captured by the enabled camera.

Here, since it is preferable that the capturing range includes the area in which the bed device 3AL is present, it is necessary that the camera device 20AL1 and the camera device 20AL2 are enabled. By enabling the camera device 20AL1 and the camera device 20AL2, the controller 100 can acquire images of the user and surroundings of the user following the movement of the user.

According to the present system 1, the camera devices 20AL1 and 20AL2 provided on the bed device 3AL can be used in cooperation with each other as compared with a normal case where only the camera device 20A1 and the camera device 20A2 provided on the bed device 3A are used. That is, the present system 1 can determine various risks based on a wider capturing range than a normal capturing range.

Figure 16A:
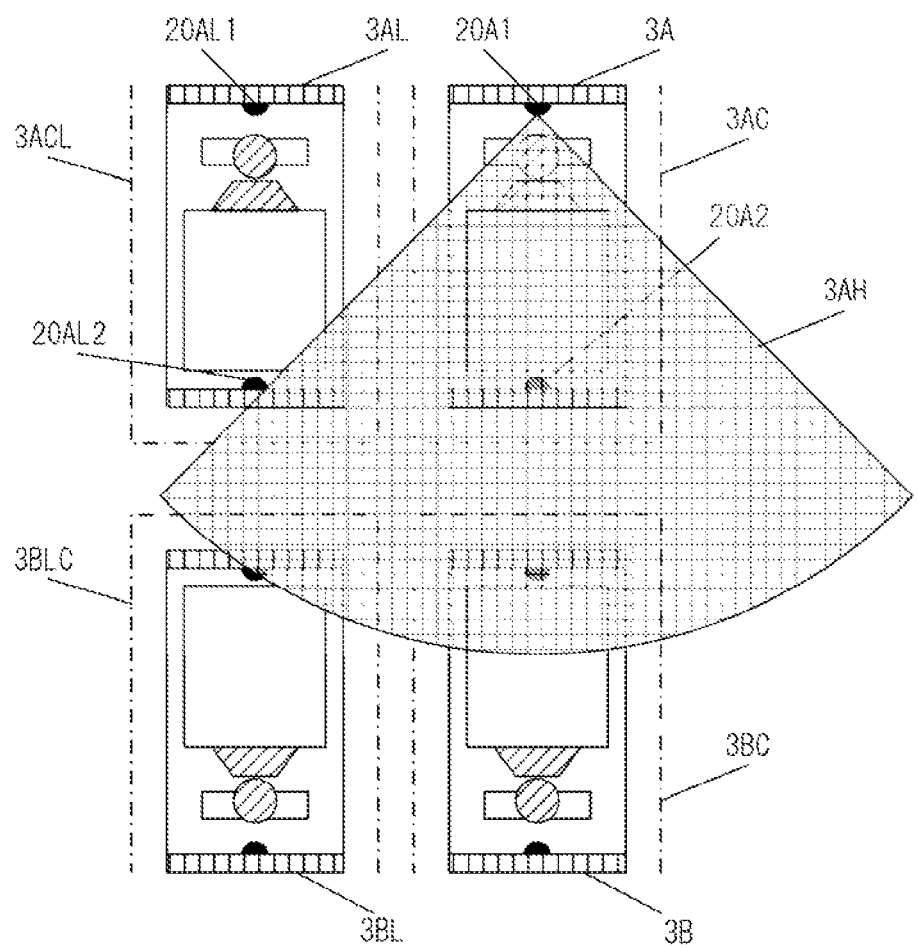
FIGS. 16A and 16B are diagrams for illustrating the operation example according to the fifth embodiment.

The capturing range, which is a range necessary for the determination of the risk described above, may be dynamically changed. For example, FIG. 16A illustrates only the bed devices 3A, 3AL, 3B, and 3BL.

At this time, a curtain may be installed surrounding each bed device 3 in order to block the field of view of other users, staffs, and the like. For example, in FIG. 16A, a curtain 3AC is installed around the bed device 3A (dashed line portion). Similarly, a curtain 3ACL is installed around the bed device 3AL. A curtain 3BC is installed around the bed device 3B. A curtain 3BLC is installed around the bed device 3BL.

The curtain can be freely opened and closed by the user, the staff, or the like. Therefore, the range that can be captured by the camera changes in accordance with the opening and closing of the curtain. For example, as illustrated in FIG. 16A, when the curtain is not closed, the range that can be captured by the camera device 20A1 is 3AH.

Figure 16B:
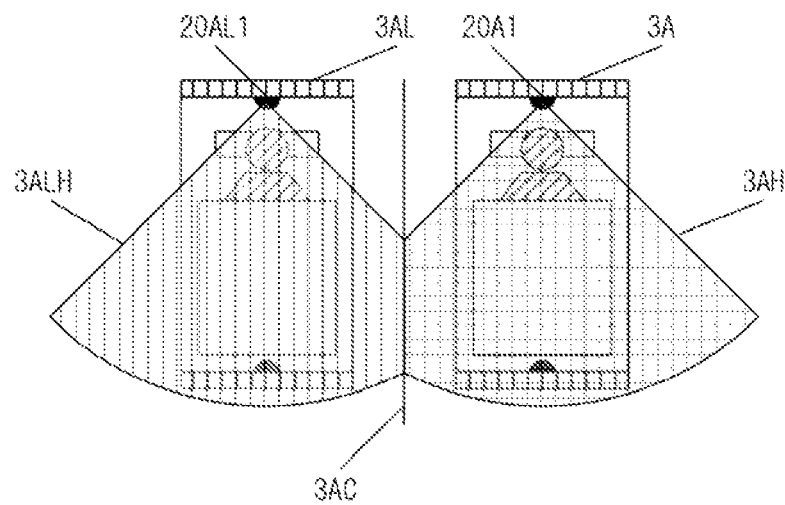

Here, a state in which the curtain is closed will be described with reference to FIG. 16B. FIG. 16B is a diagram illustrating only the bed devices 3A and 3AL. In this case, the curtain 3AC is closed between the bed device 3A and the bed device 3AL. For example, the range that can be captured by the camera device 20A1 of the bed device 3A is 3AH. Therefore, a range on the bed device 3AL side, which is a range beyond the curtain, cannot be captured, and an obstacle cannot be detected.

For example, when the user of the bed device 3A departs from the bed on the bed device 3AL side, it is not possible to appropriately capture the image. Therefore, the controller 100 acquires an image captured by the camera device 20AL1 of the adjacent bed device 3AL.

Accordingly, the controller 100 can appropriately acquire the image even in a range blocked by the curtain 3AC.

The controller 100 may obtain the state of the curtain (for example, whether the curtain is closed or the capturing range is restricted) by analyzing the acquired image or by detecting by a sensor. For example, the controller 100 may acquire the state of the curtain by analyzing the image acquired by the camera device 20 provided in the bed device 3 or the image of the living room or the hospital room captured by another camera device 20. The controller 100 may acquire the state of the curtain by providing the sensor on a curtain rail.

6. Sixth Embodiment

Figure 17:
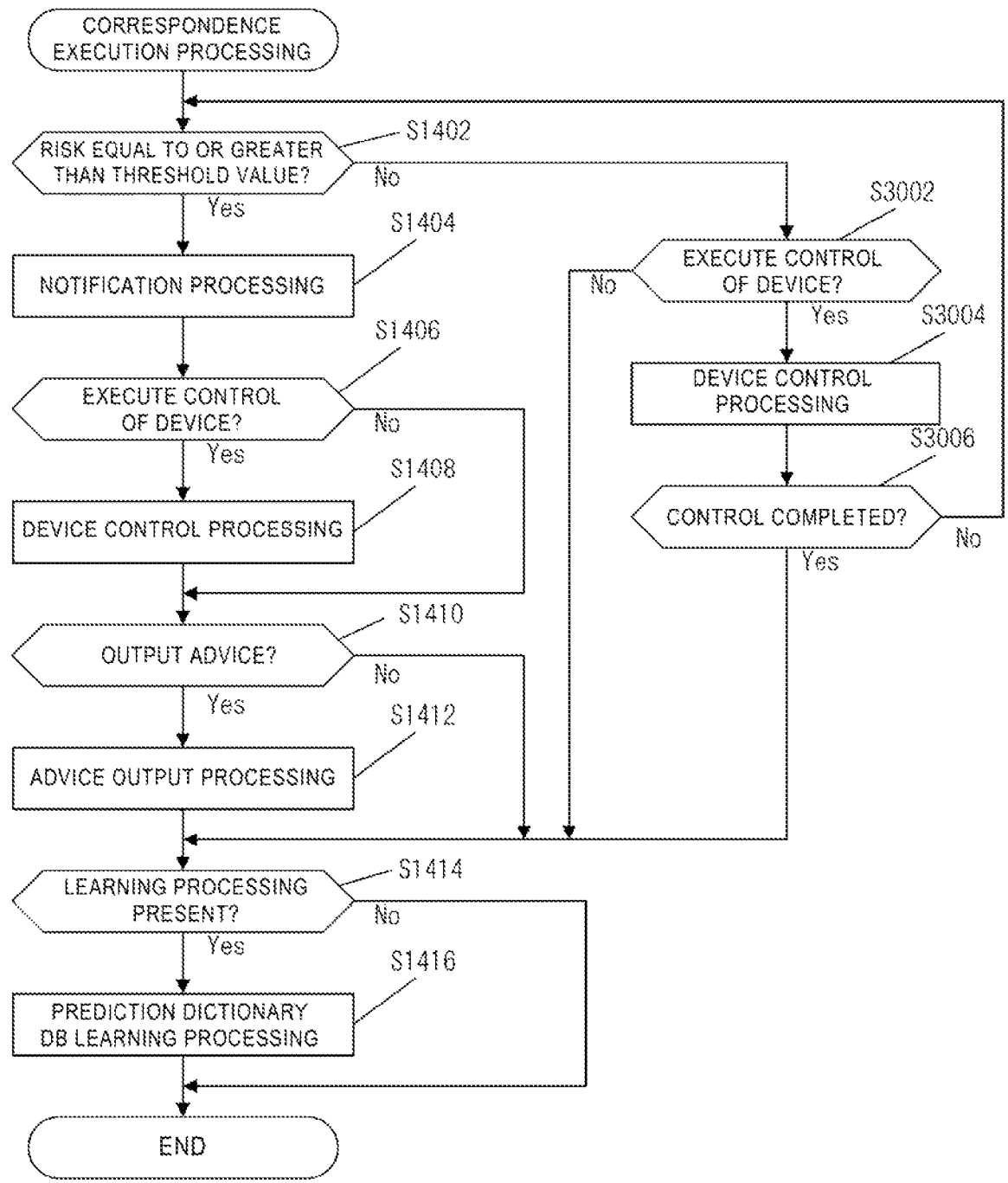
FIG. 17 is a flowchart for illustrating processing according to a sixth embodiment.

A sixth embodiment is an embodiment in which an operation mode of the bed device 3 is switched or the processing is switched according to the risk predicted by the risk prediction processing. In the present embodiment, the processing in FIG. 8 in the first embodiment is replaced with processing in FIG. 17. The same processing in FIGS. 8 and 17 are denoted by the same reference numerals, and the description thereof will be omitted.

First, when the risk is less than a threshold value (step S1402; No), the controller 100 determines whether to execute control of the device (step S3002). Here, when the control of the device is executed, the controller 100 sets an operation mode for the bed device 3 and executes the control. The control to be executed by the controller 100 can be various operations such as rotation processing, back raising, foot lowering, and kind motion.

For example, it is assumed that the bed device 3 is set to execute the rotation processing. The setting to execute the rotation processing may be, for example, when the staff or the user performs an operation to execute the rotation processing. When the user does not move for a predetermined time or more, the controller 100 may be set to execute the rotation processing.

That is, when the risk is low (for example, when possibility of overturning and falling is equal to or less than a set probability), the controller 100 executes the rotation processing (step S3002; Yes to step S3004).

When the risk is equal to or greater than the threshold value while the rotation processing is being executed (step S3006: No to step S1402; Yes), the rotation processing is stopped in step S1408.

According to the present embodiment, when the controller 100 determines that the risk of the user is high while the device is operating, the controller 100 appropriately stops the operation. When it is determined that the risk of the user is high when the device is operated, the controller 100 can implement that the device is not operated while it is determined that the risk is high.

In particular, it is effective in processing such as the rotation processing in which the risk of overturning and falling is increased by changing the position of the user.

7. Seventh Embodiment

A seventh embodiment is an embodiment in which a route is predicted as one of movements of a user to determine a risk.

In the present embodiment, in the risk prediction processing of step S1312 in FIG. 7, a route along which the user moves together with the risk of the user is predicted. For example, in the example in FIG. 18, when the controller 100 (the prediction unit 112) detects that the user P of the bed device 3A departs from the bed in a direction M1 that is at the left side, the controller 100 predicts a route M2 of the user P.

The prediction unit 112 may perform prediction in accordance with the direction in which the user P departs from the bed, a time zone, or a normal behavior. For example, since there is a doorway on the left side in FIG. 18, it is predicted that the user P walks toward the doorway.

Figure 19:
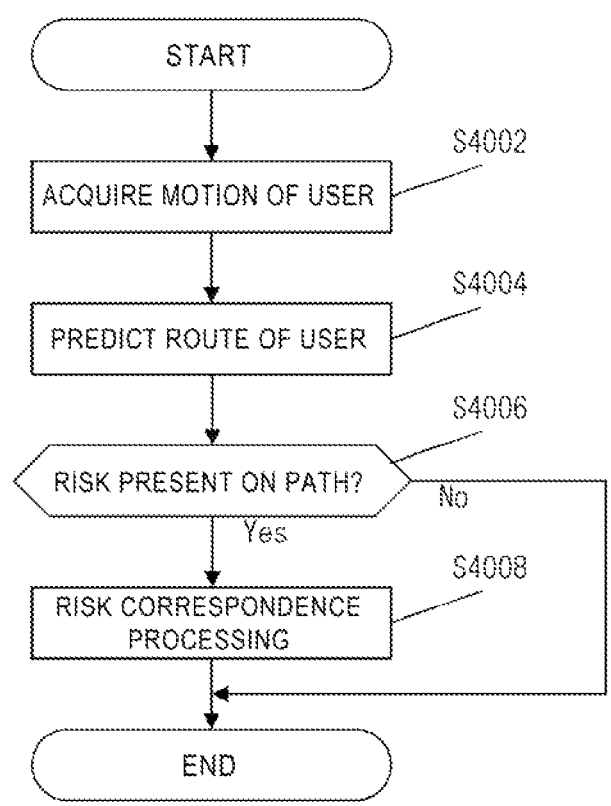
FIG. 19 is a flowchart for illustrating processing according to the seventh embodiment.

At this time, the controller 100 executes processing according to the route. For example, as illustrated in FIG. 19, the controller 100 acquires a motion of the user (step S4002). For example, the motion acquisition unit 106 acquires the motion by executing the motion acquisition processing in FIG. 6.

Subsequently, the prediction unit 112 predicts the route of the user from the acquired motion of the user (step S4004). When there is a risk on the predicted route, the controller 100 executes processing corresponding to the risk (step S4006; Yes to step S4008).

Although the prediction unit 112 predicts the route of the user in step S4004, the prediction unit 112 may predict only the place at which the next motion is to be performed. For example, in FIG. 18, it is assumed that when the controller 100 recognizes the user by using the camera device 20A1, the user is also recognized by the camera device 20AL1. In this case, the controller 100 can acquire that the user is moving in the left direction in FIG. 18.

Here, the following processing may be considered as the risk correspondence processing.
(1) Case Where Obstacle Is Present For example, when there is an obstacle on the route, it may be determined that the risk is high. That is, the controller 100 may output the risk output by executing the risk prediction processing at a higher level than usual. The presence of the obstacle includes, for example, a state in which the floor is wet.

When there is the obstacle, the controller 100 may notify the user that there is a risk. When there is the obstacle, the controller 100 may notify the staff that there is bed-departure or there is the obstacle on the route.
(2) Brightness Control The controller 100 may control the brightness for the user on the route. For example, it is assumed that the bed device 3 is provided with an illumination device such as a foot lamp.

Figure 18:
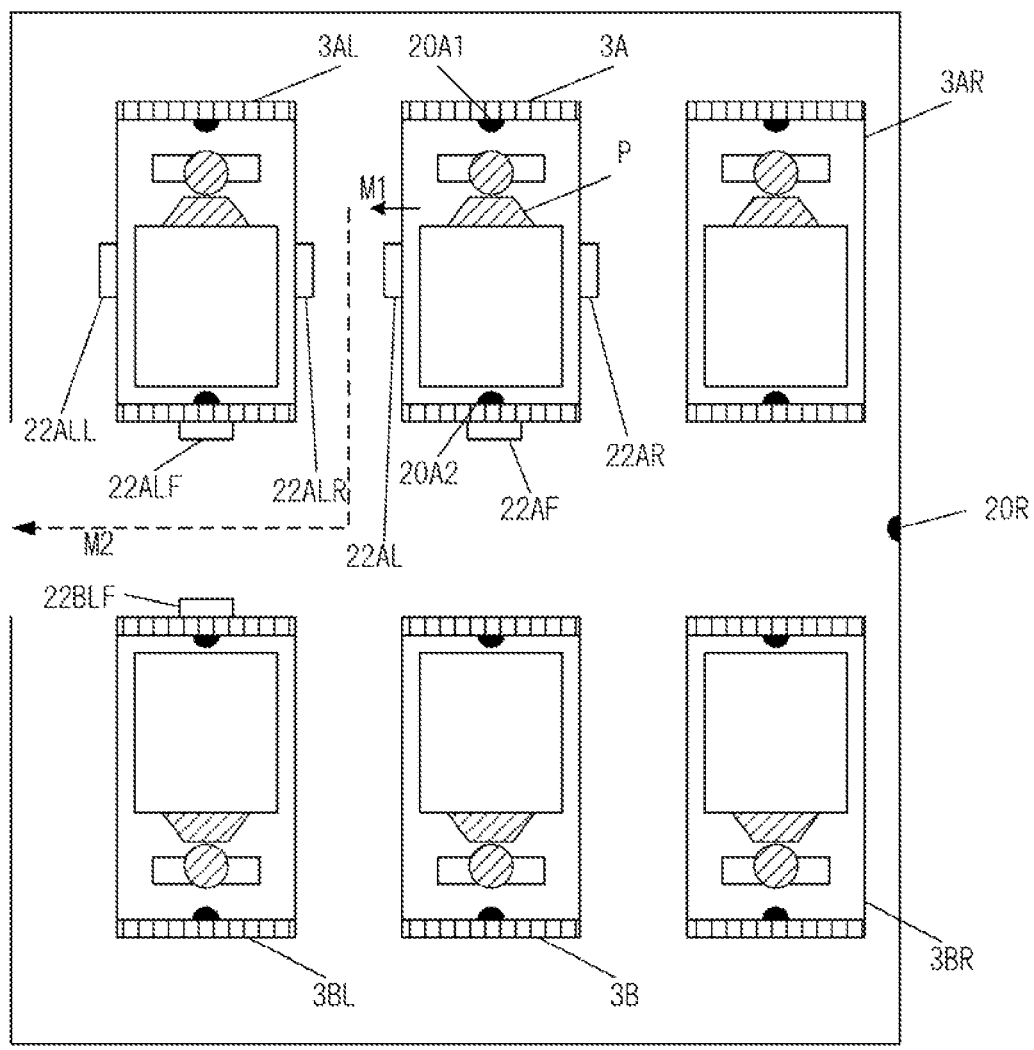
FIG. 18 is a diagram for illustrating an operation example according to a seventh embodiment.

For example, the bed device 3A in FIG. 18 is provided with a light 22AL on the left side of the drawing, a light 22AR on the right side of the drawing, and a light 22AF on the foot side. Similarly, the bed device 3AL is provided with a light 22ALL on the left side of the drawing, a light 22ALR on the right side of the drawing, and a light 22ALF on the foot side.

At this time, since the user P departs from the bed in the M1 direction, the controller 100 turns on the light 22AL. The controller 100 cooperates with the control device of the bed device 3AL (or cooperates with the illumination device) to turn on the light on the route M2. Here, the lights 22ALR and 22ALF of the bed device 3AL are turned on.

At this time, the controller 100 may also turn on a light 22BLF of the bed device 3BL. In this way, the controller 100 can adjust the brightness on the route in cooperation with the illumination device provided in another bed device 3.

The controller 100 may turn on the illumination device in advance based on the predicted route, or may turn on the illumination device when the user P approaches the vicinity of the illumination device.

[8. Eighth Embodiment]

An eighth embodiment is an embodiment in a case where notification is performed at an appropriate timing based on a risk other than overturning and falling as a risk of a user, or advice is provided to a staff or the like or the user. In the present embodiment, the prediction processing in FIG. 7 is replaced.

In the prediction processing in FIG. 7, after a position of the user is specified in step S1302, a feature amount to be used is appropriately determined in step S1304. In the present embodiment, a necessary feature amount is determined regardless of the position of the user (that is, without executing step S1302).

The following processing is executed according to, for example, the risk obtained in the risk prediction processing (step S1312).

[8.1 Hand Washing]

The controller 100 (surrounding environment acquisition unit 102) acquires a feature amount based on a motion of the staff or the like surrounding the user. Specifically, the camera device 20 captures an image of the staff other than the user and acquires the motion of the staff.

Here, information for specifying the staff (for example, a staff name, and a staff code) may be recognized based on the image captured by the camera device 20. Information for specifying the staff may be registered when the staff performs a treatment on the user via the terminal device 52 surrounding the bed device 3. As a method of registering information for specifying the staff, the staff ID or the staff name may be simply selected by the terminal device 52, or information recorded in an ID card or the like may be read and registered by a card reader or the like.

When the controller 100 acquires information indicating that the staff washes his/her hands, the controller 100 may store the information in the storage unit 120. The controller 100 may transmit the information to the server device 50. The server device 50 can manage whether or not the staff has washed the hands.

Here, whether or not the staff washes the hands may be acquired by a sensor, or may be recognized based on the image captured by the camera device 20. For example, the controller 100 may acquire information indicating that the the staff washes the hands via a wearable device worn by the staff. The controller 100 analyzes the image captured by the camera device 20 and recognizes the movement of the staff.

Then, the controller 100 may acquire the information indicating that the staff washes the hands from the recognized movement of the staff.

The information stored in the storage unit 120 or transmitted to the server device 50 by the controller 100 may include, for example, the staff name (staff ID), a time point at which the staff washed the hands, and a washing place.

Then, when a certain period of time elapses since the staff or the like washed the hands, the controller 100 may notify the staff that he/she has not washed the hands. For example, when the controller 100 recognizes that the staff or the like is approaching the bed device 3 of another user even though a certain period of time elapses since the staff or the like washed the hands, the controller 100 may notify the staff by displaying on the terminal device 52 surrounding the bed device 3. The controller 100 may notify the terminal device 52 used by the corresponding staff of the fact.

The controller 100 may perform the notification in accordance with not only the time but also the state of the user. For example, when the user who is treated by the staff is involved in infection, the controller 100 may notify the staff or the like before and after the treatment.

As described above, according to the embodiment described above, by performing the notification based on the hand washing, it is possible to reduce the risk of infection such as infection with the staff or infection with the user.

When the camera device 20 is used, the controller 100 can acquire and notify information indicating whether or not the staff or the like has washed the hands in conjunction with the camera device 20 without using an additional device or a sensor.

For example, the controller 100 can acquire, from the camera device 20, whether or not a family member or a person who visits the hospital to see the user other than a doctor or a medical staff washes his/her hands.

[8.2 Equipment Management]

The controller 100 (the surrounding environment acquisition unit 102) acquires a feature amount based on a position of the equipment (including a movement auxiliary tool), presence or absence of use of the equipment, and presence or absence of wiping of the equipment.

Then, the controller 100 may store the acquired position of the equipment, the presence or absence of use, and the presence or absence of wiping in the storage unit 120. The controller 100 may transmit information including the position of the equipment, the presence or absence of use, and the presence or absence of wiping to the server device 50.

The server device 50 may acquire and manage a use situation and an arrangement situation of the equipment in the facility transmitted from the control device 10. When the server device 50 receives the notification that the staff brings the equipment, the server device 50 can also notify the staff of the position of the equipment that is close to the position of the staff and is not used.

The staff can grasp more appropriate equipment by grasping the use situation of the equipment in the facility. Accordingly, it is possible to quickly provide the user with necessary equipment, and it is possible to avoid, for example, a risk of slowing down the correspondence to the user.

[8.3 Movement of Bed Device]

The controller 100 (the surrounding environment acquisition unit 102) acquires a feature amount based on the state of the bed device 3. Then, the controller 100 determines whether or not the state of the bed device 3 is a state that causes a risk, and appropriately notifies the fact or gives advice to the staff or the like. For example, after the bed device 3 is moved, the controller 100 performs the notification when the staff does not take an appropriate behavior.

For example, it is assumed that a power supply to the control device 10 is switched from an AC power supply to a battery power supply in order to move the bed device 3. The surrounding environment acquisition unit 102 acquires the surrounding environment based on the image captured by the camera device 20.

Here, when the bed device 3 does not move after the power supply is switched to the battery power supply, the surrounding environment acquisition unit 102 determines that the switching to the AC power supply is forgotten (a power supply adapter is forgotten to be inserted into an outlet), and notifies the staff or the like.

Here, some methods can be considered for determining that the bed device 3 does not move. For example, the controller 100 determines that the bed device 3 does not move when the image captured by the camera device 20 is not changed or when a rate of change is small. When there is no or little change in a value (acceleration) acquired by the sensor device 30 (for example, an acceleration sensor), the controller 100 determines that the bed device 3 does not move.

As described above, it is possible to determine, as the risk, that the staff does not switch the power supply from the battery power supply to the AC power supply even though the staff finishes moving the bed device 3, and to perform notification via the notifying unit 140.

[8.4 Equipment Remaining Amount]

The controller 100 (the surrounding environment acquisition unit 102) determines that there is the risk when equipment around the bed device 3 is in a predetermined situation.

The controller 100 acquires a remaining amount of infusion attached to an IV stand/IV pole as a feature amount based on the image captured by the camera device 20. Here, when it is determined that the amount of infusion is equal to or less than a threshold value, it may be notified that the risk is high. The controller 100 may also notify a type of infusion to be supplemented at this time. The controller 100 may notify the staff in charge of the user that the remaining amount of infusion is small.

[9. Modification]

Although the embodiments have been described in detail with reference to the drawings, the specific configuration is not limited to the embodiments, and a design or the like within a scope not departing from the gist of the present embodiment is also included in the scope of the claims.

A program that operates in each device in the embodiments is a program that controls a CPU or the like (a program that causes a computer to function) so as to implement the functions of the embodiments described above. Information handled by these devices is temporarily stored in a temporary storage device (for example, RAM) at the time of processing, and then stored in storage devices such as various ROMs, HDDs, and SSDs, and read, modified, and written by the CPU as needed.

When the program is distributed to the market, the program may be stored in a portable recording medium and distributed, or may be transferred to a server computer connected via a network such as the Internet. In this case, it goes without saying that the storage device of the server computer is also included in the present embodiment.

The embodiments described above can also be implemented by, for example, a smartphone or a tablet. For example, a staff or the like places the smartphone on the foot board of the bed device 3, and captures an image of the bed device 3 with a camera built in the smartphone. The sensor device 30, the bed control device 40, and the like acquire information by being connected by short-distance wireless communication.

By installing an application capable of implementing the functions implemented by the controller 100 in the smartphone, it is possible to implement the system in the above-described embodiments on the smartphone.

In the above-described embodiments, the notification processing includes various methods as processing of notifying the user and/or the staff. For example, the controller 100 may notify that there is a risk by displaying the risk on the display 130. The controller 100 may perform notification by using notification methods such as alarm sound, sound, light, and vibration from the notifying unit 140. The controller 100 may notify other terminal devices via the communicator 150. The controller 100 may perform notification via a nurse call system via the communicator 150. That is, the control device 10 outputs an alert to the user or a person other than the user.

Here, the display 130 and the notifying unit 140 through which the controller 100 performs notification may be provided in another device. For example, the notification including the display may be performed in the terminal device on the bed device 3 side, the terminal device in a nurse station, or the terminal device that can be confirmed by a doctor. The terminal device may be a stationary device or a portable device. The portable device may be, for example, a telephone including a smartphone or the like, or an information terminal device such as a tablet or the like.

The terminal device to be notified may be switched according to a degree of risk predicted by the prediction unit 112. For example, when the controller 100 determines that the risk is extremely high (the probability of overturning and falling is higher than a first threshold value), the controller 100 notifies a first terminal device (for example, the mobile terminal device 54) that the staff can see and a second terminal device on the bed device 3 side. When it is determined that the risk is high (the probability of overturning and falling is higher than a second threshold value but lower than the first threshold value), the controller 100 notifies only the second terminal device. In this manner, the controller 100 may switch a notification destination depending on the degree of the risk.

In the above-described embodiments, each piece of information may be acquired from an image captured by the camera device 20 using a learned model. Specifically, the camera device 20 recognizes the motion and the state of the object using the model. For example, the surrounding environment acquisition unit 102, the posture acquisition unit 104, the motion acquisition unit 106, and the biological information acquisition unit 108 each acquire necessary information using the image captured by the camera device 20 and the learned model.

For example, the controller 100 inputs the image (signal) captured by the camera device 20 to a neural network including a plurality of layers and neurons included in each layer. Each neuron receives a signal from a plurality of different neurons and outputs the calculated signal to the other plurality of neurons. When the neural network has a multilayer structure, the layers are referred to as an input layer, an intermediate layer (hidden layer), and an output layer in an order in which the signals flow.

A neural network whose intermediate layer includes a plurality of layers is referred to as a deep neural network, and a method of machine learning using the deep neural network is referred to as deep learning. A convolutional neural network having a convolution operation provides high accuracy in image recognition.

An image is subjected to various operations (convolution operation, pooling operation, normalization operation, matrix operation, and the like) on the neurons in each layer of the neural network, flows while changing the shape, and a plurality of signals are output from the output layer.

A plurality of output values from the neural network correspond to the position of the object, the motion of the user, the posture of the user, and the biological information of the user based on a largest output value. The controller 100 recognizes various kinds of information from the image captured by the camera device 20 by using the output value. The output value from the neural network may be recognized from the output of a classifier by passing the plurality of output values through the classifier without being directly associated with the operation or the like.

The controller 100 may learn parameters that are coefficients used for various calculations of the neural network. For example, the controller 100 inputs a large number of images to the neural network in advance, and labels indicating what the object and the state of the user captured in the image are. Then, the controller 100 may learn an error between the output value and a correct value by propagating the error through the neural network in a reverse direction by an error back propagation method (back propagation) and updating the parameters of the neurons in each layer many times.

In this case, even if the sensor device 30 is not connected, the control device 10 can acquire appropriate information by using the neural network using the learned model with only the image captured by the camera device 20.

Apart from the above embodiments, the prediction processing executed by the prediction unit 112 may be changed as follows. An example of a case where the prediction processing is executed will be described with reference to FIG. 20.

[User Inside Bed Device 3]

In this case, the prediction unit 112 determines the following points as feature amounts to be used, and acquires the determined feature amounts (steps S1304 and S1306 in FIG. 7).

(1) Surrounding Environment

The prediction unit 112 acquires, from the surrounding environment acquisition unit 102, a state of the side rail 6 as a feature amount. The state of the side rail 6 is determined based on whether or not the side rail 6 is installed, the type of the side rail 6, the installation place of the side rail 6, and the like. The prediction unit 112 acquires, from the surrounding environment acquisition unit 102, a state of the board 5 (foot board/head board) as a feature amount. The state of the board 5 is determined based on whether or not the board 5 is installed. Here, as the pattern of using the camera device 20 in the system 1, the pattern b, the pattern c, the pattern d, and the like among the patterns described with reference to FIGS. 2A to 2D may be used.

(2) Posture

The prediction unit 112 acquires, from the posture acquisition unit 104, a feature amount for the center of gravity of the user or the position of the head of the user. Here, as the pattern of using the camera device 20 in the system 1, the pattern b, the pattern c, the pattern d, and the like among the patterns described with reference to FIGS. 2A to 2D may be used.

(3) Motion

The prediction unit 112 acquires, from the motion acquisition unit 106, feature amounts as to whether or not the user is stretching his/her hand and whether or not the user is performing a motion of attaching and detaching the side rail 6 as a motion of the user. Here, as the pattern of using the camera device 20 in the system 1, the pattern b, the pattern c, the pattern d, and the like among the patterns described with reference to FIGS. 2A to 2D may be used.

(4) Reduction Factor

If there is a reduction factor, the prediction unit 112 acquires the reduction factor in the prediction processing (step S1308; Yes to step S1310). For example, the following may be considered as the reduction factor.

First, regardless of the state of the side rail 6, when the user is sleeping in a correct posture, it is determined that there is a reduction factor for the side rail 6.

Regardless of whether or not the board 5 is installed, when the user is sleeping in the correct posture or the side rail 6 is appropriately installed, it is determined that the risk caused by the absence of the board 5 is low.

Even when a motion that the user stretches his/her hand is detected as the motion of the user, when a surrounding object (for example, an object grasped by the user) is close or the user is sleeping in the correct posture, it is determined that there is a reduction factor for the motion of the user (the motion that the user stretches his/her hand).

[Case Where User Is Standing]

In this case, the prediction unit 112 determines the following points as feature amounts to be used, and acquires the determined feature amounts (steps S1304 and S1306 in FIG. 7).

(1) Surrounding Environment

The prediction unit 112 acquires, from the surrounding environment acquisition unit 102, a state of the casters 7 as a feature amount. The state of the casters 7 is determined based on, for example, a direction of the casters 7, or a lock state. The prediction unit 112 acquires, from the surrounding environment acquisition unit 102, a state of the equipment surrounding the bed as a feature amount. The state of the equipment surrounding the bed is determined based on the presence or absence, the type, and the like of the equipment arranged surrounding the bed device 3. Here, as the pattern of using the camera device 20 in the system 1, the pattern a, the pattern d, and the like among the patterns described in FIGS. 2A to 2D may be used.

(2) Motion

The prediction unit 112 acquires, from the motion acquisition unit 106, feature amounts as to whether the user is shaking, whether the user is performing a motion of removing the side rail 6, or whether the user is walking with socks (slippers) as the motion of the user. Here, as the pattern of using the camera device 20 in the system 1, the pattern b, the pattern c, the pattern d, and the like among the patterns described with reference to FIGS. 2A to 2D may be used. Whether the user is walking with socks (slippers) may be determined by using the pattern a, the pattern d, and the like among the patterns described in FIGS. 2A to 2D in the system 1.

(3) Reduction Factor

If there is a reduction factor, the prediction unit 112 acquires the reduction factor in the prediction processing (step S1308; Yes to step S1310). For example, the following may be considered as the reduction factor.

Regardless of the state of the casters 7, when a standing posture of the user is appropriate, a transfer destination to which the user transfers is locked, or an object that the user grasps is appropriately arranged, it is determined that there is the reduction factor for the casters 7.

In this manner, when it is determined that there is the reduction factor for the casters 7, the prediction unit 112 outputs the risk at a level lower than the level of the originally output risk of overturning and falling, or at a probability lower than the originally output probability of overturning and falling.

[Case Where User Is in Sitting Position in Bed Device 3]

In this case, the prediction unit 112 determines the following points as feature amounts to be used, and acquires the determined feature amounts (steps S1304 and S1306 in FIG. 7).

(1) Surrounding Environment

The prediction unit 112 acquires, from the surrounding environment acquisition unit 102, the floor height of the bed device 3 (a section of the bed device 3 or a ground height of the mattress 4) as a feature amount. The prediction unit 112 acquires, from the surrounding environment acquisition unit 102, a state of the assistance bar as a feature amount. The prediction unit 112 acquires a state of equipment surrounding the bed device 3 as a feature amount. The state of the equipment surrounding the bed device 3 is determined based on, for example, the type of the equipment, the state of the equipment, and the position of the equipment. The prediction unit 112 acquires a state of a sensor provided in the bed device 3 as a feature amount. The state of the sensor is determined based on, for example, the presence or absence of installation of the sensor, the type of the sensor, and a value output from the sensor.

Here, various patterns of using the camera device 20 in the system 1 are conceivable. For example, in order to acquire the floor height of the bed device 3 and the state of the equipment surrounding the bed device 3, the pattern a, the pattern d, and the like among the patterns described with reference to FIGS. 2A to 2D may be used in the system 1. In order to acquire the state of the assistance bar, the pattern b, the pattern c, the pattern d, and the like among the patterns described with reference to FIGS. 2A to 2D can be used in the system 1. In order to acquire the state of the sensor, the pattern a, the pattern b, the pattern c, the pattern d, and the like among the patterns described with reference to FIGS. 2A to 2D can be used in the system 1.

(2) Posture

The prediction unit 112 acquires, from the posture acquisition unit 104, feature amounts for the position of the hand of the user, as to whether or not the foot of the user is on the floor, and whether or not the user is sitting deeply (positions of the waist and the hip). Here, as the pattern of using the camera device 20 in the system 1, the pattern b, the pattern c, the pattern d, and the like among the patterns described with reference to FIGS. 2A to 2D may be used. In order to acquire whether or not the foot of the user is on the floor, the pattern a, the pattern d, and the like among the patterns described with reference to FIGS. 2A to 2D may be used in the system 1.

(3) Motion

The prediction unit 112 acquires, from the motion acquisition unit 106, feature amounts as to whether or not the user is carrying out the motion of wearing footwear, whether or not the user is trying to pick up an object at a distant place, and whether or not the user is carrying out the motion of removing the side rail 6 as the motion of the user. Here, as the pattern of using the camera device 20 in the system 1, for the motion of the user wearing the footwear, the pattern a, the pattern d, and the like among the patterns described with reference to FIGS. 2A to 2D may be used. As the pattern of using the camera device 20 in the system 1, for the motion of whether or not the user is trying to pick up the object at the distant place, the pattern d or the like among the patterns described with reference to FIGS. 2A to 2D may be used. As the pattern of using the camera device 20 in the system 1, for the motion of removing the side rail 6, the pattern b, the pattern c, the pattern d, and the like among the patterns described with reference to FIGS. 2A to 2D may be used.

(4) Reduction Factor

If there is a reduction factor, the prediction unit 112 acquires the reduction factor in the prediction processing (step S1308; Yes to step S1310). For example, the following may be considered as the reduction factor.

Regardless of the state of the assistance bar, when the posture of the user at the sitting position is appropriate, it is determined that there is a reduction factor for the state of the assistance bar.

Regardless of the state of the equipment surrounding the bed device 3, when the posture of the user at the sitting position is appropriate, it is determined that there is a reduction factor for the state of the equipment surrounding the bed device 3.

Regardless of the state of the position of the hand of the user, when the object surrounding the bed device 3 is close and the user is sleeping in the appropriate posture, it is determined that there is a reduction factor for the position of the hand.

Regardless of the motion that the user tries to pick up the object at the distant place, when the object surrounding the bed device 3 is close and the user is sleeping in the appropriate posture, it is determined that there is a reduction factor for the motion that the user tries to pick up the object at the distant place.

While certain embodiments have been described, these embodiments have been presented by way of example only, and are not intended to limit the scope of the disclosures. Indeed, the novel embodiments described herein may be embodied in a variety of other forms; furthermore, various omissions, substitutions and changes in the form of the embodiments described herein may be made without departing from the spirit of the disclosures. The accompanying claims and their equivalents are intended to cover such forms or modifications as would fall within the scope and spirit of the disclosures.

What is claimed is:

1. A bed system comprising:
    a first bed including a first imaging device attached to the first bed;
    a second bed including a second imaging device attached to the second bed; and
    a controller configured to: detect a motion of a first patient, predict a location which the first patient using the first bed would reach based on the motion of the first patient, specify the second imaging device which is capable of capturing an image of the location, and activate the second imaging device if the controller determines that the first imaging device is not capable of monitoring the first patient based on the location of the first patient and the second imaging device is capable of monitoring the first patient.

2. The bed system according to claim 1, wherein the controller is configured to specify the scope of monitoring of the first imaging device after determining the location of the first patient.

3. The bed system according to claim 1, wherein the controller includes a first unit to acquire environment information from the first or second imaging device, a second unit to acquire a posture of the first patient from the first or second imaging device, a third unit to acquire a motion of the first patient the first or second imaging device, a fourth unit to acquire biological information of the first patient from a sensor which is provided on the bed and is different from the first or second imaging device, a fifth unit to acquire disease information of the first patient from a server.

4. The bed system according to claim 3, wherein the controller is configured to predict a possibility of falling of the first patient in accordance with information acquired from the first and fifth units.

5. The bed system according to claim 1, wherein the bed includes a bed board, and the first imaging device is installed on upper side of a bed board.

6. He bed system according to claim 3, wherein the controller is configured to change parameters to be acquired from the first to fifth units based on the location of the first patient, the location indicating whether the first patient is in the bed or not, whether the first patient is sitting on the edge of the bed or not.

7. The bed system according to claim 6, wherein the controller is configured to acquire information related to whether or not a side rail of the bed is installed or whether a bed board is installed as environment information when the first patient is in the bed.

8. The bed system according to claim 6, wherein the controller is configured to acquire information related to a state of the castor or whether there is equipment surrounding the bed as environment information when the first patient is standing outside the bed.

9. The bed system according to claim 6, wherein the controller is configured to acquire information related to a bed height of the bed or whether the sensor is provided on the bed as environment information when the first patient is sitting on the edge of the bed.

10. A method for use with a bed system including a first bed including a first imaging device attached to the first bed, a second bed including a second imaging device attached to the second bed, and a controller, the method comprising:

with the controller, detecting a motion of a first patient, predicting a location which the first patient using the first bed would reach based on the motion of the first patient, specifying the second imaging device which is capable of capturing an image of the location, and activating the second imaging device if the controller determines that the first imaging device is not capable of monitoring the first patient based on the location of the first patient and the second imaging device is capable of monitoring the first patient.

11. The method according to claim 10, further comprising specifying the scope of monitoring of the first imaging device after determining the location of the first patient.

12. The method according to claim 10, further comprising performing a first unit process of acquiring environment information from the first or second imaging device, a second unit process of acquiring a posture of the first patient from the first or second imaging device, a third unit process of acquiring a motion of the first patient the first or second imaging device, a fourth unit process of acquiring biological information of the first patient from a sensor which is provided on the bed and is different from the first or second imaging device, a fifth unit process of acquiring disease information of the first patient from a server.

13. The method according to claim 12, further comprising predicting a possibility of falling of the first patient in accordance with information acquired from the first and fifth unit processes.

14. The method according to claim 10, wherein the bed includes a bed board, and the first imaging device is installed on upper side of a bed board.

15. The method according to claim 12, further comprising changing parameters to be acquired from the first to fifth unit processes based on the location of the first patient, the location indicating whether the first patient is in the bed or not, or whether the first patient is sitting on the edge of the bed or not.

16. The method according to claim 15, further comprising acquiring information related to whether or not a side rail of the bed is installed or whether a bed board is installed as environment information when the first patient is in the bed.

17. The method according to claim 15, further comprising acquiring information related to a state of the castor or whether there is equipment surrounding the bed as environment information when the first patient is standing outside the bed.

18. The method according to claim 15, further comprising acquiring information related to a bed height of the bed or whether the sensor is provided on the bed as environment information when the first patient is sitting on the edge of the bed.

* * * * *